US012753386B2

(12) United States Patent
Lin et al.

(10) Patent No.: US 12,753,386 B2
(45) Date of Patent: Oct. 6, 2026

(54) PRODUCTION METHOD FOR STAGE 5 NEURONS

(71) Applicants: Waka Lin, Tokyo (JP); Hikaru Watanabe, Kanagawa (JP); Shusaku Shiomoto, Kanagawa (JP)

(72) Inventors: Waka Lin, Tokyo (JP); Hikaru Watanabe, Kanagawa (JP); Shusaku Shiomoto, Kanagawa (JP)

(73) Assignee: Ricoh Company, Ltd., Tokyo (JP)

( * ) Notice: Subject to any disclaimer, the term of this patent is extended or adjusted under 35 U.S.C. 154(b) by 530 days.

(21) Appl. No.: 18/332,209

(22) Filed: Jun. 9, 2023

(65) Prior Publication Data

US 2023/0399611 A1 Dec. 14, 2023

(51) Int. Cl.
*C12N 5/0793* (2010.01)

(52) U.S. Cl.
CPC ........ *C12N 5/0619* (2013.01); *C12N 2503/02* (2013.01); *C12N 2506/45* (2013.01)

(58) Field of Classification Search
None
See application file for complete search history.

(56) References Cited

U.S. PATENT DOCUMENTS

2020/0300835 A1 9/2020 Lin et al.

FOREIGN PATENT DOCUMENTS

JP 2020-156463 10/2020
WO WO-2008118421 A1 * 10/2008 ............. A61P 25/00

OTHER PUBLICATIONS

Lesuisse, Christian; Martin, Lee J; "Long-Term Culture of Mouse Cortical Neurons as a Model for Neuronal Development, Aging, and Death" Journal of neurobiology, 5, 9-23, 2002 (Year: 2002).*

Kaech,Stefanie; Banker, Gary; "Culturing hippocampal neurons" Nature Protocols, 1, 2506-2415, 2006 (Year: 2006).*

Bianchi, Fabio; et al; "Rapid and efficient differentiation of functional motor neurons from human iPSC for neural injury modelling" Stem Cell Research, 32, 126-134, 2018 (Year: 2018).*

Harrill, Joshua A; et al; "Media formulation influences chemical effects on neuronal growth and morphology" In Vitro Cellular Developmental Biology-Animal, 51, 612-629, 2015 (Year: 2015).*

Extended Search Report dated Dec. 4, 2023, for European Patent Application No. 23178688.0, 10 pages.

Miura et al., "Generation of human striatal organoids and cortico-striatal assembloids from human pluripotent stem cells", Nature Biotechnology, vol. 38, No. 12, 3 Dec. 3, 2020, XP037311079, pp. 1421-1430, with Extended Data.

Gunhanlar et al., "A simplified protocol for differentiation of electrophysiologically mature neuronal networks from human induced pluripotent stem cells", Molecular Psychiatry, vol. 23, No. 5, Apr. 18, 2017, XP055492651, pp. 1336-1344.

Lee et al., "Production of human spinal-cord organoids recapitulating neural-tube morphogenesis", Nature Biomedical Engineering, Nature Publishing Group UK, London, vol. 6, No. 4, Mar. 28, 2022, XP037806941, pp. 435-448, with Extended Data.

(Continued)

*Primary Examiner* — David W Berke-Schlessel
(74) *Attorney, Agent, or Firm* — Grüneberg Global IP, PLLC

(57) ABSTRACT

A production method for stage 5 neurons with mature dendrites includes culturing stage 3 neurons with immature dendrites in a culture medium containing B-27 Plus.

6 Claims, 31 Drawing Sheets

(56) References Cited

OTHER PUBLICATIONS

Wilson et al., "Protocol for Evaluating Neuronal Polarity in Murine Models", Star Protocols, vol. 1, No. 3, Dec. 18, 2020, XP93098977, pp. 1-19.
Lin et al., "Dendritic spine formation and synapse maturation in transcription factor-induced human iPSC-derived neurons", iScience, Apr. 21, 2023, XP093097683, 23 pages.
Togo K. et al., "Postsynaptic structure formation of human iPS cell-derived neurons takes longer than presynaptic formation during neural differentiation in vitro", Mol Brain, vol. 14, No. 149, 2021, pp. 1-17.

* cited by examiner

PRODUCTION METHOD FOR STAGE 5 NEURONS

BACKGROUND OF THE INVENTION

Field of the Invention

The present invention relates to a production method for stage 5 neurons. More specifically, the present invention relates to a production method for stage 5 neurons, stage 5 neurons, and a method for screening a therapeutic drug for neurological disease. The present application claims priority on Japanese Patent Application No. 2022-095627, filed on Jun. 14, 2022, Japanese Patent Application No. 2022-178783, filed on Nov. 8, 2022, and Japanese Patent Application No. 2023-030877, filed on Mar. 1, 2023, the contents of which are incorporated herein by references.

Description of Related Art

In the field of regenerative medicine and drug discovery for neurological diseases, expectations are high for a technology that induces the differentiation of human nerve cells (neurons) from pluripotent stem cells. In particular, although various methods for inducing the differentiation of induced pluripotent stem cells (iPSCs) into neurons have been established, the processes and conditions under which these neurons acquire functional maturity are largely unknown.

It has been reported that in a case where iPSC-derived neurons are subjected to long-term culture for tens to hundreds of days, electrophysiological functions appear spontaneously. In particular, it is known that the formation of dendritic spines receiving neurotransmission signals and a postsynaptic region (postsynapse), and excitatory responses mediated by postsynaptic NMDA receptors, are often incomplete in the iPSC-derived neurons (see, for example, Non-Patent Document 1).

It is known that excitatory postsynapses in the brain are formed in spines, which are cellular microstructures, on the dendrites of a neuron, and their morphological and functional maturation plays an important role in higher brain functions such as cognition and learning. For example, drebrin serving as an actin-binding protein is used as a marker for the formation and dynamics of spines. Drebrin is classified into two isoforms such that an embryonic isoform E, which is expressed in juvenile neurons, is present in a neurite growth cone, and is converted into an adult-type isoform A (brain-type drebrin) through splicing in a mature neuron to be assembled as granules (clusters) at the dendritic spines.

In addition, the localization change of drebrin by excitatory responses mediated by the NMDA receptors is an important mechanism of synaptic plasticity. In in vivo or in primary cultured rodent cells, the expression of a drebrin cluster is used as an evaluation marker for synaptic disorders in neuro-excitotoxicity and neurodegenerative diseases.

In principle, the formation of spines containing a drebrin cluster is expected even in fully matured human iPSC-derived neurons. However, in fact, the existence of spines that can exhibit functional maturity by localization changes in drebrin or the like has not been reported in human iPSC-derived neurons. It has been suggested that it is difficult to obtain human iPSC-derived neurons exhibiting such functional maturity (see, for example, Non-Patent Document 1).

In particular, the development of alternative methods using human iPSC-derived neurons and the development of drug discovery screening technologies related to synaptic disorder demand a highly stable method for producing mature neurons suitable for industrial practical use.

SUMMARY OF THE INVENTION

In general, neurons that have some neuron-specific markers expressed and that electrically fire are often referred to as mature neurons. However, according to this definition, stage 3 neurons whose dendrites are immature and whose postsynapses are not functioning may be included in mature neurons.

A distinction is made herein between "stage 3 neurons with immature dendrites" and "stage 5 neurons with mature dendrites".

The differentiation and maturation process of neurons in in vitro culture is strictly divided into the following five stages (see Dotti C., et al. The establishment of polarity by hippocampal neurons in culture, J. Neurosci., 8, 1454-1468, 1988., Arimura N, and Kaibuchi K., Neuronal polarity: From extracellular signals to intracellular mechanisms, Nat. Rev. Neurosci., 8, 194-205, 2007., and the like).

Stage 1: A state in which there are no neurites and filopodia are present immediately after seeding.

Stage 2: A state in which immature neurites with growth cones at the tips begin to elongate. A distinction between dendrites and axons has not yet been made.

Stage 3: A state in which neuronal polarization has occurred, and one immature neurite has elongated to become an axon. Other immature neurites remain short. At this point, the distinction between the dendrites and axons can be made based on the fact that the axons express, for example, tau (MAPT) and neurofilament (NF), and that the immature neurites becoming dendrites express microtubule-associated protein 2 (MAP2).

Stage 4: A state in which the dendrites begin to be elongated and branched, and then matured after the axons have grown to some extent.

Stage 5: A state in which spines are formed on the mature dendrites and neurotransmission and synaptic plasticity through chemical synapses are achieved.

FIG. 1 is a schematic diagram showing a differentiation and maturation process of an iPSC-derived neuron hypothesized by the inventors. It was hypothesized that the differentiation and maturation process of the iPSC-derived neuron follows the five stages described above. FIG. 1 also shows localization change of drebrin. Neurons at stage 1 to stage 5 in the present specification an distinguished based on the differentiation and maturation process shown in FIG. 1.

As shown in FIG. 1, a stage 1 neuron is a neural progenitor cell that does not yet have neurites. A stage 2 neuron shows the initiation of neurite elongation. In addition, drebrin E (details will be described later) is present around the cell body and in the growth cone at the tip of the elongating neurite. Neuronal polarization occurs in a stage 3 neuron. The dendrites can be distinguishable from the axons, and neurogenesis has been completed, but both the morphology and function are immature. A stage 4 neuron initiates dendrite maturation (elongation and branching) and synaptogenesis. In a stage 5 neuron, dendrites are matured, and drebrin A (which will be described in detail later) aggregates granularly to form spines and stable postsynaptic structures.

Human iPSC-derived neurons are known to reach stage 3 relatively easily, at which dendrites are still immature.

However, as described above, it is difficult to mature human iPSC-derived neurons to stage 5 where dendritic spines and postsynapses are formed.

In Non-Patent Document 1, a post-synaptic maturation evaluation method of differentiating human iPSCs into neural progenitor cells, inducing the neural progenitor cells to be differentiated into neurons, and using brain-type drebrin as an indicator is disclosed.

It is described in Non-Patent Document 1 that in order to truly mature human iPSC-derived neurons, it is necessary to confirm not only the expression of gene markers observed in stages 3 and 4 and the assessment of a presynaptic region (presynapse), but also the formation of spines and postsynapses.

However, in the neurons described in Non-Patent Document 1, the expression of brain-type drebrin clusters is very low (4 to 5 cells per cell) and clusters of Postsynaptic density protein 95 (PSD95), which serves as a postsynaptic marker, were not present, and electrophysiological assessment using a multipoint electrode array failed to show synaptic transmission activity. Thus, Non-Patent Document 1 did not succeed in producing stage 5 neurons with structurally and functionally mature dendrites.

An object of the present invention is to provide a technology for maturing stage 3 neurons with immature dendrites into stage 5 neurons with dendritic spines and postsynapses.

A production method for stage 5 neurons with mature dendrites according to the present invention includes a step of culturing stage 3 neurons with immature dendrites in a culture medium containing B-27 Plus.

According to the present invention, it is possible to provide a technology for maturing stage 3 neurons with immature dendrites into stage 5 neurons with dendritic spines and postsynapses formed.

BRIEF DESCRIPTION OF THE DRAWINGS

FIG. 98 is a graph showing the top 20 significantly enriched gene ontology terms for a cluster DOWN2 in Experimental Example 4.

FIG. 11C is a graph showing the top 20 significantly enriched gene ontology terms for a cluster UP3 in Experimental Example 4.

DETAILED DESCRIPTION OF THE INVENTION

[Method for Producing Stage 5 Neurons]

Figure 1:
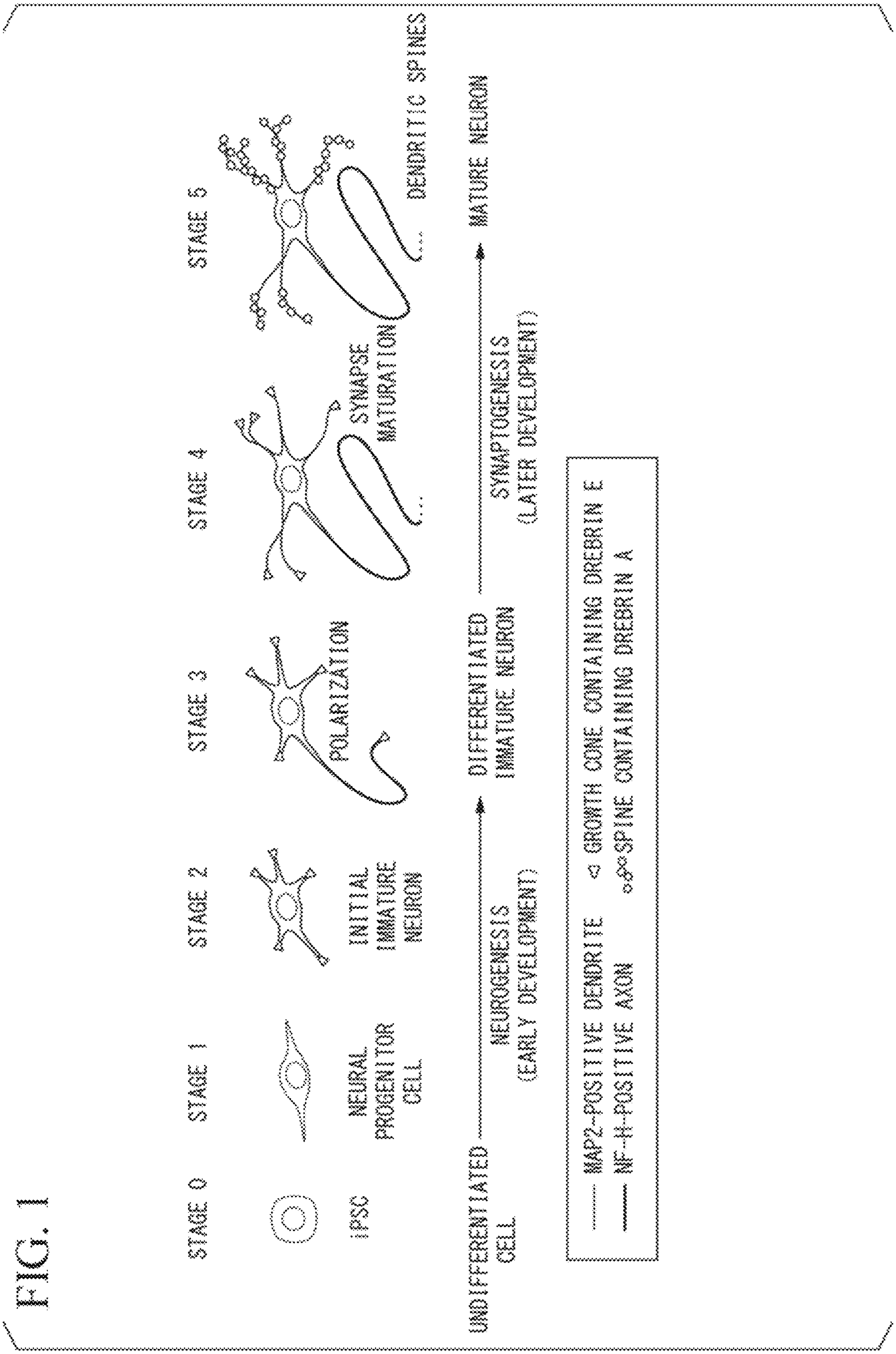
FIG. 1 is a schematic diagram showing a differentiation and maturation process of an iPSC-derived neuron.

In an embodiment, the present invention provides a production method for stage 5 neurons with mature dendrites including a step of culturing stage 3 neurons with immature dendrites in a culture medium containing B-27 Plus.

As will be described later in Examples, according to the production method of the present embodiment, the stage 3 neurons with immature dendrites can be matured into stage 5 neurons with dendritic spines and postsynapses formed. Therefore, it can be said that the production method of the present embodiment is a method for inducing maturation of stage 3 neurons into stage 5 neurons.

B-27 Plus is a supplement used to culture nerve cells, and is added to a basal medium for usage. B-27 Plus is sold by Thermo Fisher Scientific Inc., Principal components of 8-27 Plus are shown in Table 1 below.

TABLE 1

| Component |
|---|
| Biotin |
| DL-α-tocopherol acetic acid |
| DL-α-tocopherol |
| Vitamin A |
| Bovine Serum Albumin, Fraction V, Fatty Acid Free |
| Catalase |
| Human recombinant insulin |
| Human transferrin |
| Superoxide dismutase |
| Corticosterone |
| D-galactose |
| Ethanolamine hydrochloride |
| Reduced glutathione |
| L-carnitine hydrochloride |
| Linoleic acid |
| Linolenic acid |
| Progesterone |
| Putrescine dihydrochloride |
| Sodium selenite |
| T3 (triodo-I-thyronine) |

In the production method of the present embodiment, a basal medium to which B-27 Plus is added can be used as a culture medium.

The basal medium is not particularly limited, and any serum-free basal medium for cell culture can be used. Examples of the basal medium include a synthetic medium buffered at pH 7.2 or higher and pH 7.6 or lower and other culture medium. More specifically, examples of the basal medium include NeuroBasal medium (Thermo Fisher Scientific Inc.), NeuroBasal Plus medium (Thermo Fisher Scientific Inc.), BrainPhys medium (Stem Cell Technologies), a nerve cell medium containing a culture supernatant of rat glial cell (FUJIFILM Wako Pure Chemical Corporation), Advanced-Dulbecco's Modified Eagle's medium/Ham's F-12 mixed medium (DMEM/F12), RPMI1640 medium, Advanced RPM) medium, and other medium.

B-27 Plus is preferably added to the basal medium in an amount of, for example, 0.1% by volume or more, 0.5% by volume or more, 1% by volume or more, or 1.5% by volume or more. The amount of B-27 Plus added to the basal medium may be, for example, 10% by volume or less, 8% by volume or less, 6% by volume or less, 4% by volume or less, 3% by volume or less, or 2% by volume or less. These upper and lower limits can be combined optionally. For example, B-27 Plus may be added to the basal medium in an amount of 0.1% by volume or more and 10% by volume or less, 0.5% by volume or more and 5% by volume or less, 1% by volume or more and 3% by volume or less, or 2% by volume.

Additives other than B-27 Plus may be added to the culture medium. Examples of such additives include CultureOne (Thermo Fisher Scientific Inc.), GlutaMAX (Thermo Fisher Scientific Inc.), ascorbic acid, antibiotics, N-2 supplements, cytostatic agents such as DAPT and Ara-C, growth factors such as BDNF, GDNF, and IGF-1.

As described later in Examples, stage 5 neurons can be produced by culturing stage 3 neurons in a culture medium containing 13-27 Plus for, for example, 50 days or longer, 60 days or longer, 70 days or longer, 80 days or longer. There is no upper limit to the culture time, but for example, 12 months or shorter, 10 months or shorter, 8 months or shorter, or 6 months or shorter is practical.

In the production method of the present embodiment, the stage 3 neurons preferably express neuronal markers including MAP2 and neurofilament heavy chain (NF-H) and are preferably polarized. Furthermore, the stage 3 neurons are preferably obtained by differentiation induction of pluripotent stem cells.

As will be described later in Examples, the production method of the present embodiment is particularly effective in a case of using a transcription factor induction method that enables highly efficient production of stage 3 neurons directly from pluripotent stem cells via no neurosphere. That is, the stage 3 neurons am preferably induced to differentiate by induction of expression of a transcription factor in the pluripotent stem cells.

The induction of expression of a transcription factor in pluripotent stem cells may be performed by transfecting mRNA of the transcription factor into cells, by using an RNA virus such as a Sendai virus vector, by introducing a gene construct that induces expression using a DNA virus such as a lentiviral vector, or by introducing a gene construct that induces expression using genetic modification such as genome editing. In particular, it is preferable to induce expression by using mRNA transfection or RNA virus because there is no risk of exogenous genes being integrated into a genome and remaining in the genome for a long period of time.

Examples of pluripotent stem cells include embryonic stem cells (ESCs), induced pluripotent stem cells (iPSCs), and the like. The pluripotent stem cells are preferably mammalian-derived cells. Examples of mammals include rodents such as mice, rats, hamsters, and guinea pigs; ungulates such as pigs, cows, goats, horses, and sheep; carnivorous animals such as dogs and cats; primates such as human, rhesus monkeys, cynomolgus monkeys, marmosets, orangutans, chimpanzees; and other mammals.

The pluripotent stem cells are preferably human cells. In addition, the pluripotent stem cells may be wild-type cells, cells derived from neurological disease patients, genetically modified wild-type cells, or other cells.

In the production method of the present embodiment, dendritic spines are formed in the stage 5 neurons. In addition, it is preferable that a postsynaptic structure including drebrin and PSD95 be formed in the stage 5 neurons.

[Stage 5 Neurons]

In one embodiment, the present invention provides stage 5 neurons derived from human iPS cells with mature dendrites, which have been isolated and cultured in a container, "Isolated and cultured" means, for example, not mature neurons or the like present in a tissue section.

In the related art, no successful in vitro production of functional stage 5 neurons with dendritic spines and postsynapses in human iPSC-derived cells has been reported.

In contrast, as will be described later in Examples, the inventors were the first to succeed in in vitro production of stage 5 neurons with dendritic spines and postsynapses formed, derived from human iPSCs.

Stage 5 neurons of the present embodiment can be produced in vitro from stage 3 neurons by the method described above. Therefore, the stage 5 neurons of the present embodiment are isolated and cultured in a container.

The container is not particularly limited, and those commonly used for cell culture can be used. More specific examples of the container include dishes, multiwell plates, glass slides, planar microelectrode arrays (MEAs), and the like.

The stage 5 neurons of the present embodiment are preferably cultured in planar culture (2D culture) or spheroid culture (3D culture. In addition, it is preferable that the stage 5 neurons of the present embodiment consist of nerve cells, and that other cells are not contained therein.

That is, the stage 5 neurons of the present embodiment are distinguished from brain organoids and the like that contain a plurality of cells and are 3D cultured.

[Method for Screening Therapeutic Drug for Neurological Disease]

In one embodiment, the present invention provides a method for screening a drug including a step of assessing a function or phenotype of stage 5 neurons induced to differentiate from neurological disease patient-derived iPSCs in the presence and/or absence of a test substance. Stage 5 neurons can typically be obtained by the method described above. As a way of assessing the function or phenotype in the presence and/or absence of the test substance, for example, in a maturation stage from stage 3 neurons to stage 5 neurons or after maturation to stage 5 neurons, the function or phenotype is assessed with comparison between a case in which the stage 5 neurons have been exposed to the test substance or have not been exposed to the test substance.

The test substance is not particularly limited, and for example, natural compound libraries, synthetic compound libraries, existing drug libraries, or the like can be used.

The function or phenotype of stage 5 neurons is not particularly limited, and examples thereof include dendrite maturity, electrophysiological properties, and the like. Examples of the maturity of dendrites include shapes of dendritic spines, the presence or absence of formation of postsynaptic structures, shapes of postsynaptic structures, the localization of drebrin, the localization of PSD95, and the like. Examples of the electrophysiological properties include the number of electrical activity detection electrodes, spontaneous firing, synchronized network burst frequency, electrically dependent calcium influx, drug effects on these, and the like. Examples of the drugs include potassium channel inhibitors, N-methyl-D-aspartic acid (NMDA) receptor inhibitors, α-amino-3-hydroxy-5-mesoxazole-4-propionic acid (AMPA) receptor inhibitor, agonists and antagonists of various neurotransmitter substances (for example, glutamic acid and the like), and the like.

As neurological disease patient-derived iPSCs, iPSCs prepared from cells derived from neurological disease patients, iPSCs into which the same gene mutation as in neurological disease patients is introduced, and the like can be used.

In a case in which the function or phenotype of the stage 5 neurons in the presence of the test substance exhibits a phenotype more similar to a wild-type as compared with a phenotype of the stage 5 neurons in the absence of the test substance, it is determined that the test substance is a candidate if a therapeutic drug for neurological disease. In contrast, in a case in which the function or phenotype of the stage 5 neurons in the presence of the test substance more strongly expressed characteristics of the disease as compared with the phenotype of the stage 5 neurons in the absence of the test substance, it is determined that the test substance is a candidate of causative substances for neurological disease or substances that promote the disease.

First Embodiment

In a screening method according to a first embodiment, exposure to the test substance is performed at the maturation stage from stage 3 neurons to stage 5 neurons. In a case in which a candidate of a therapeutic drug for neurological disease is obtained by the screening method of the present embodiment, the therapeutic drug is administered before stage 3 neurons mature into stage 5 neurons. Therefore, it is expected that the expression of a phenotype of the neurological disease can be prevented. That is, it is considered that a candidate compound obtained by the screening method of the present embodiment may be used as a prophylactic drug for neurological disease.

Second Embodiment

In a screening method according to a second embodiment, exposure to the test substance is performed after maturation to stage 5 neurons. Therefore, the screening method according to the second embodiment differs from the screening method according to the first embodiment mainly in the timing at which the test substance is allowed to act.

In the screening method according to the first embodiment, the test substance is allowed to act in the step of obtaining the stage 5 neurons from the stage 3 neurons, whereas in the screening method according to the second embodiment, after obtaining the stage 5 neurons, the test substance is allowed to act.

In the screening method according to the second embodiment, the test substance, the phenotype of the stage 5 neurons, the neurological disease patient-derived iPSCs, and other components are the same as in the screening method according to the first embodiment.

In the screening method according to the second embodiment, the pre-determined period of time for culturing stage 5 neurons in the presence of the test substance is not particularly limited, and for example, may be one minute or longer, 3 minutes or longer, 5 minutes or longer, 10 minutes or longer, 30 minutes or longer, 1 hour or longer, one day or longer, 3 days or longer, one week or longer, 2 weeks or longer, one month or longer, 3 month, or longer, and the like. The predetermined period of time for culturing stage 5 neurons in the presence of the test substance may be, for example, 3 months or shorter, one month or shorter, one week or shorter 3 days or shorter, one day or shorter, 12 hours or shorter, 6 hours or shorter, one hour or shorter, 30 minutes or shorter, 10 minutes or shorter, and the like. These upper and lower limits can be combined optionally. The predetermined period of time for culturing stage 5 neurons in the presence of the test substance may be, for example, one minute, 3 minutes, 5 minutes, or 10 minutes, 30 minutes, one hour, 6 hours, 12 hours, about one day, about one week, or about one month.

In a case in which a candidate of the therapeutic drug for neurological disease is obtained by the screening method according to the second embodiment, it can be expected that the therapeutic drug can be administered to stage 5 neurons that have already exhibited a phenotype of the neurological disease, resulting in a more normal phenotype capable of being treated.

EXAMPLES

Experimental Example 1

(Examination of Neurons Induced to Differentiate from iPSCs by Induction of Expression of Transcription Factor)

Human iPSC-derived neurons (product name "Quick-Neuron (trademark) Excitatory-Hunan iPSC-derived Neurons", ELIXIRGEN SCIENTIFIC, INC.) were cultured and shapes thereof were observed. These neurons were cryopreserved 3 days after introduction of tRNA of a transcription factor, which promotes the induction of differentiation to neurons, into iPSCs.

The human iPSC-derived neurons were thawed, suspended in a culture medium recommended by the manufacturer, and seeded in a 96-well culture plate precoated with 0.05% polyethyleneimine (PEI, Sigma-Aldrich) and a 20 μg/mL laminin solution (Sigma-Aldrich) at a cell density of 50,000 cells/cm$^2$.

Day 0 was defined as the day when a transcription factor was introduced into iPSCs, and the induction of differentiation was initiated. Since the cryopreservation was performed on Day 3, the next day after thawing and seeding was designated as Day 4. Half of the culture medium was replaced every 3 to 4 days from Day 4. On any day from Day 4 to Day 10, half of the culture medium was replaced with a culture medium obtained by adding 2% of B-27 Plus (Thermo Fisher Scientific Inc.), 10% of a nerve cell medium (FUJIFILM Wako Pure Chemical Corporation), 1% of CultureOne (Thermo Fisher Scientific Inc.), 1% of GlutaMAX (Thermo Fisher Scientific Inc.), 0.1% of 200 mM ascorbic acid, 1% of antibiotic (Penicillin Streptomycin) to Neurobasal Plus basal medium (Thermo Fisher Scientific Inc.).

Figure 2:
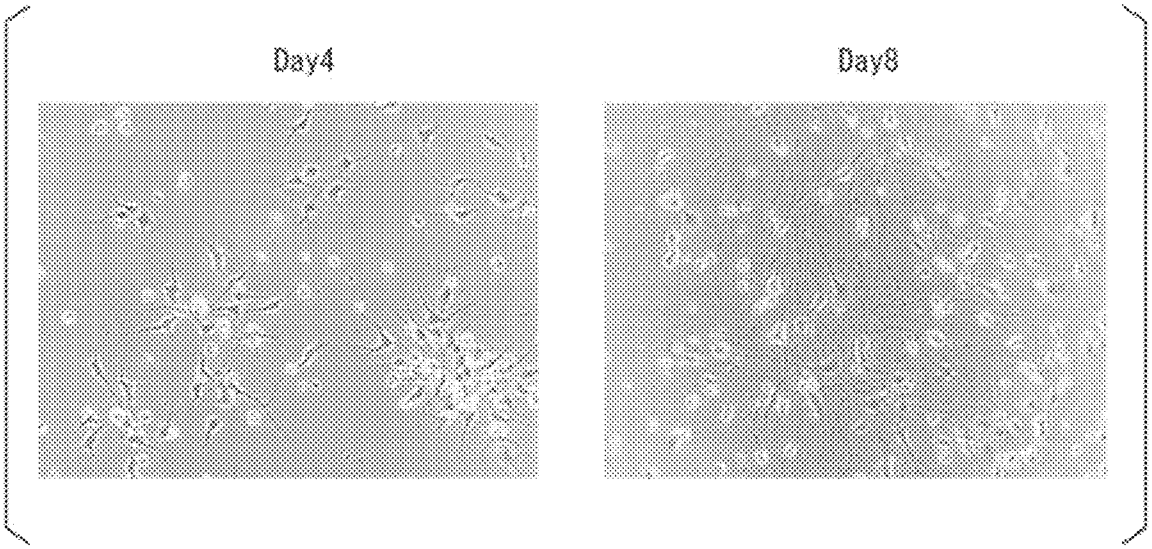
FIG. 2 is phase contrast microscope images showing the result of Experimental Example 1.

FIG. 2 is phase contrast microscope images of cells on day 1 (Day 4) and day 8 after seeding. Scale bar is 100 μm. As a result, it was confirmed that neurites began to elongate on Day 4 and that long axons were formed on Day 8.

On Days 10, 37, and 71, the cells were fixed with paraformaldehyde and immunostained to examine the expression of MAP2 serving as a dendrite marker and the expression of neurofilament heavy chain (NF-H) serving as an axon marker. Nuclei were also stained with DAPI.

Figure 3:
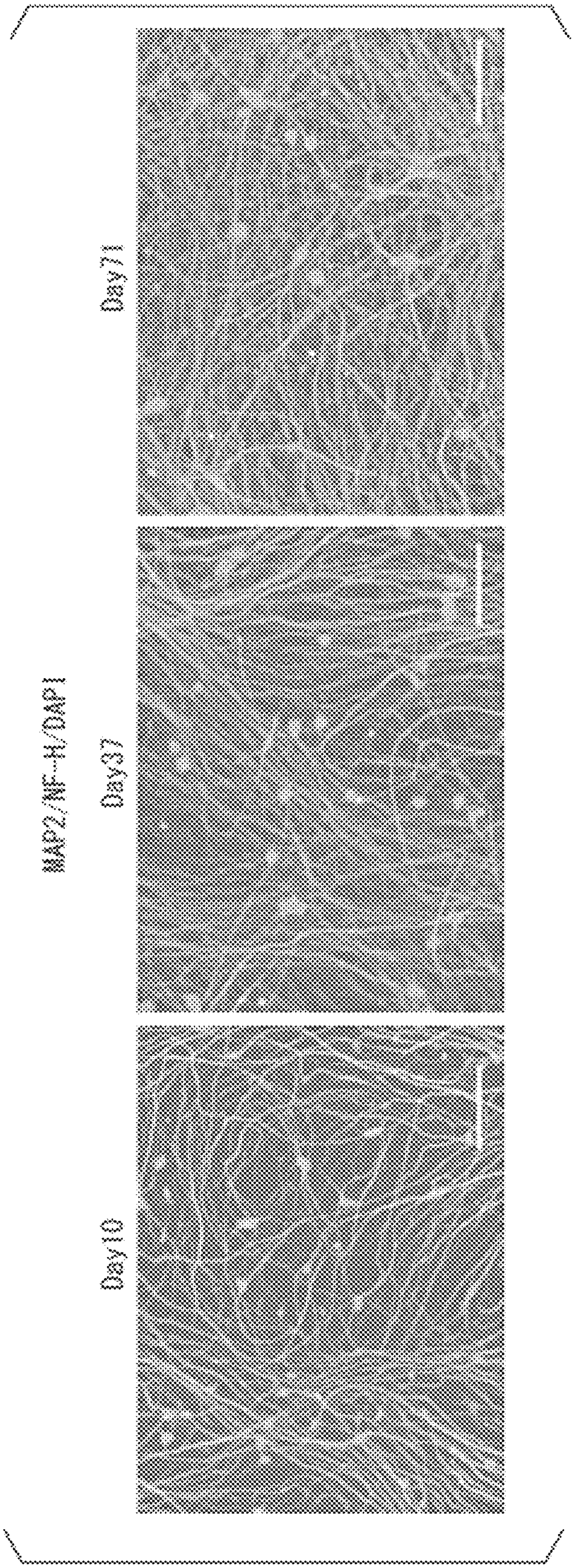
FIG. 3 shows representative fluorescence microscope images representing the results of immunostaining in Experimental Example 1.

FIG. 3 shows representative fluorescence microscope images representing the results of immunostaining. Scale bar is 100 μm. As a result, it was shown that on Day 10 of the early stage of culture, cell bodies expressed MAP2, but dendrites were hardly developed at this stage. In addition, it was observed that a single long neurite elongated in each cell, and an NF-H-positive axon was formed on the extension. From the above results, it was found that at Day 10, the neurons were in a state of stage 3 neurons in which neuronal polarity was formed. On Day 37 of the later stage of culture, it was shown that neurofilament heavy chain (NF-H) positive axons developed, and MAP2-positive dendrites elongated and branched. It was shown on Day 71 that more MAP2-positive dendrites elongated and branched. From the above results, it was found that at Day 71, the neurons reached a stage after the stage 3 neurons on Day 10.

Experimental Example 2

(RNA-Seq Analysis 1)

Human iPSC-derived neurons (product name "Quick-Neuron (trademark) Excitatory-Human iPSC-derived Neurons", ELIXIRGEN SCIENTIFIC, INC.) were cultured in the same manner as in Experimental Example 1, and subjected to RNA-Seq analysis. However, for easy handling of a large number of cells, the human iPSC-derived neurons were seeded in a non-adherent U-bottom 96-well culture plate at a cell density of 10,000 cells/well to form spheroids.

The RNA-Seq analysis was performed on Day 0, Day 10, Day 32, Day 57, and Day 88. For control Day 0, two independently cultured undifferentiated iPSCs (iPSC-1 and iPSC-2) were analyzed.

Figure 4:
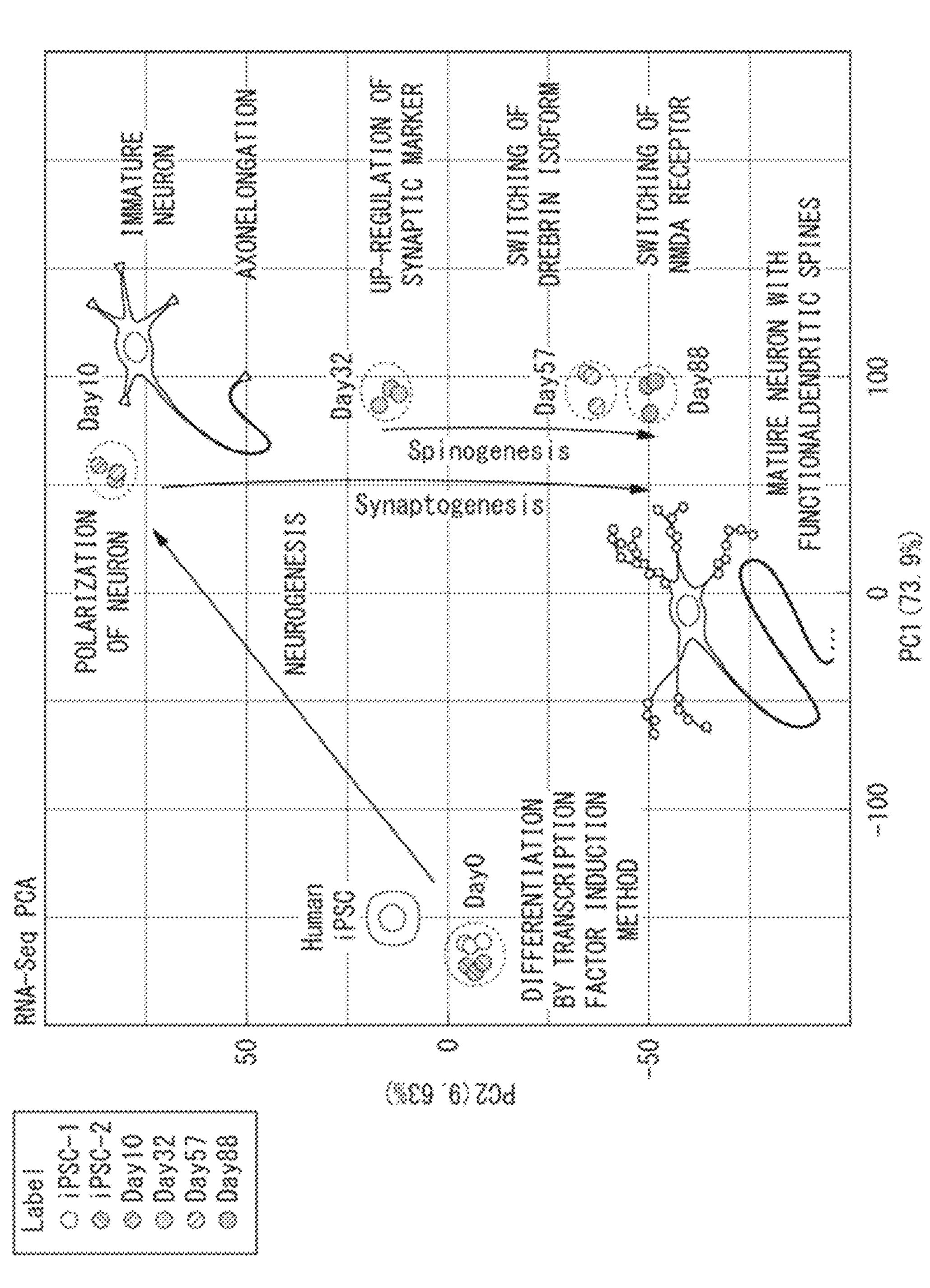
FIG. 4 is a graph showing the result of analysis on principal components in Experiential Example 2.

FIG. 4 is a graph showing the result of analysis on principal components. As a result, two trajectories of rapid differentiation from immature iPS cells and maturation requiring long-term culture were shown.

Directions of differentiation into individual cell types were estimated by plotting a mean vector of factor loadings of cell type-specific marker genes. A set of the cell type-specific marker genes was acquired front Polioudakis D., et al., A Single-Cell Transcriptomic Atlas of Human Neocortical Development during Mid-gestation, Neuron 103, 785-801, 2019. For the given cell types, an average corresponding factor loading was defined as a differentiation direction V (PC1, PC2) calculated based on Equation (1) below.

$$V(PC1, PC2) = \frac{\sum_{i=0}^{n} G_i(PC1, PC2)}{n} \tag{1}$$

[In Equation (1), V represents the differentiation direction vector, G represents the PC1/PC2 factor loading vector, i represents the cell type marker gene, and n represents the total number of cell type marker genes.]

Figure 5:
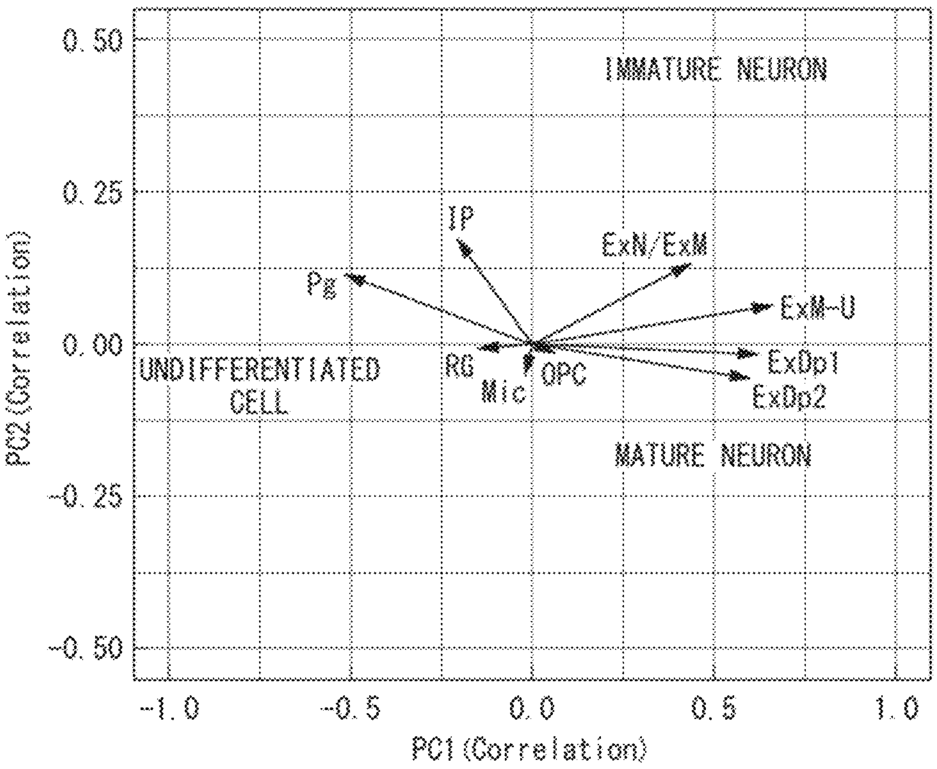
FIG. 5 is a graph showing a mean vector of individual cell types prepared in Experimental Example 2.

FIG. 5 is a graph showing the mean vectors for individual cell types. In FIG. 5, "Pg" represents proliferating immature cells, "IP" represents intermediate progenitor cells, "ExN" represents migrating excitatory neurons, "ExM" represents maturing excitatory neurons, "ExM-U" represents enriched excitatory neurons in the cortex's upper-layer, "ExDp1" represents an excitatory deep layer 1, "ExDp2" represents an excitatory deep layer 2, "RG" represents radial glia, "Mic" represent-s microglia and "OPC" represents oligodendrocyte progenitor cells.

As a result, it was shown that the cells on Day 0 were nearly proliferating immature cells (Cycling Progenitor), and the cells on Day 10 were in an intermediate state between intermediate progenitor cells and migrating excitatory neurons/maturing excitatory neurons, and the cells on Day 32 were nearly enriched excitatory neurons in the cortex's upper-layer, and the cells on Days 57 to 88 were in a state of nearly mature neurons in the excitatory deep layer.

This result indicates that although the termination of a cell cycle and neurogenesis are completed on Day 10, the neurons change to be in a more mature state over time thereafter. In addition, the result also indicates that the state of the neurons changes stepwise after Day 32, including the switching of drebrin isoforms and the switching of NMDA receptor subunits, which are characteristic molecular events of spine formation and postnatal brain development described later.

Similar experiments were performed by using human iPSC-derived neurons that have been cultured on a plane. As a result, it was shown that even in a case in which human iPSC-derived neurons were cultured on a plane, the trajectories were similar to that in the case of spheroid culture, and the human iPSC-derived neurons reached the lower right position on Day 88. It was shown from these results that neurons matured similarly in both spheroid culture and planar culture.

Figure 6:
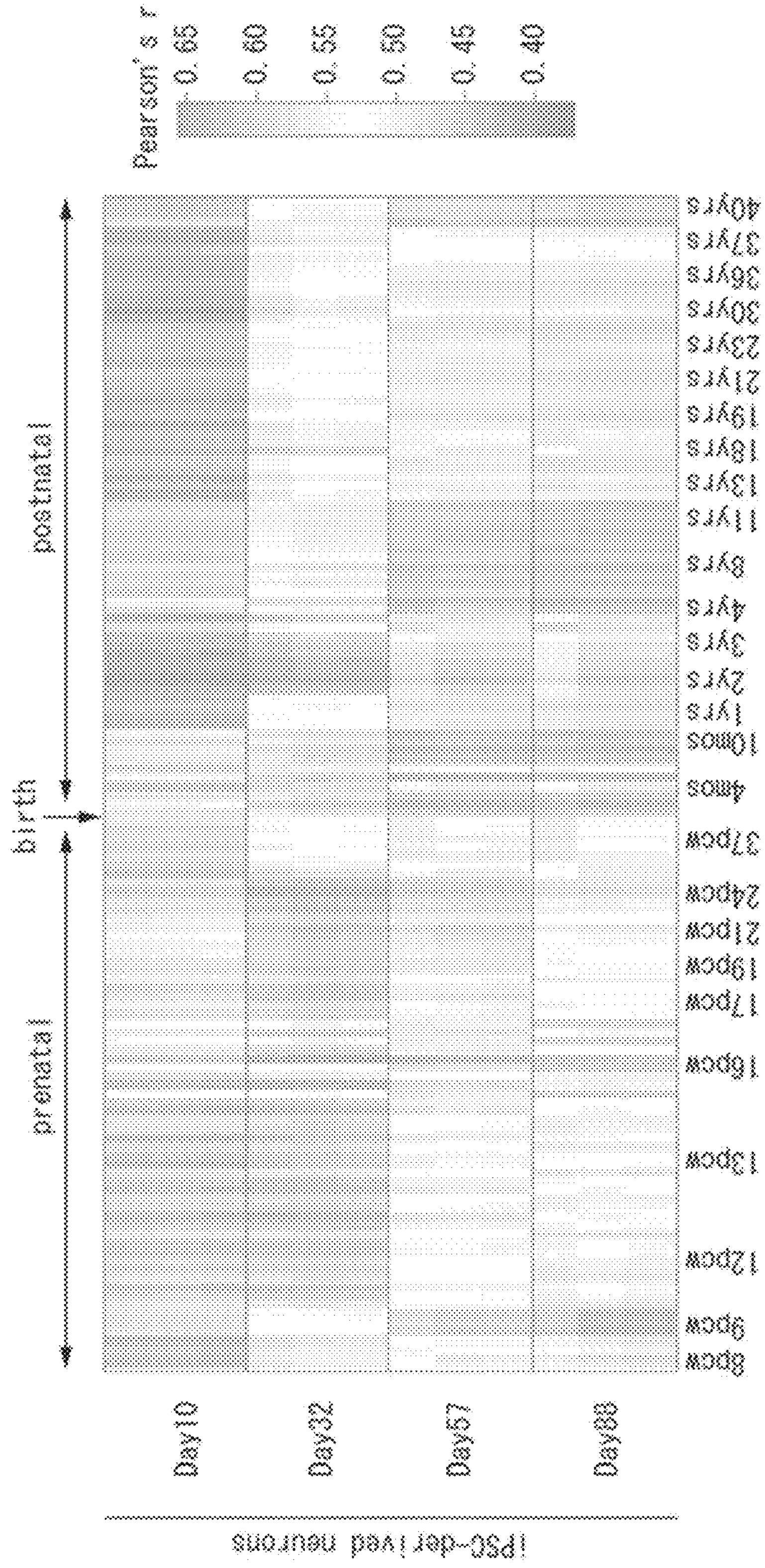
FIG. 6 is a heat map showing the result of analyzing a correlation with a developmental process of a human brain in Example 2.

Subsequently, RNA-Seq data acquired in the present Experimental Example was used to determine a correlation between Brainspan data and a time axis. Brainspan is a public database that summarizes comprehensive analyses of gene expression in human embryonic and postnatal brain development brainspan.org, Li M., et al., Integrative functional genomic analysis of human brain development and neuropsychiatric risks, Science 362, 139-148, 2018). FIG. 6 is a heat map showing a Pearson correlation coefficient between global gene expression of human iPSC-derived neurons from Days 10 to 88 and global gene expression of the human prefrontal cortex at each time period. As a result, it was found that there was a high correlation with the prenatal brain state up to Day 32 (8 to 24 weeks after conception), and a high correlation with the postnatal brain state after Day 57 (postnatal 4 months to 40 years).

Furthermore, it was found that on Day 88, the correlation with before birth was lowered, and transition to postnatal cranial nerves occurred.

Therefore, it was found that the cells up to Day 32 contain many immature stage 3 neurons similar to the fetal brain, transition to more mature stage 5 neurons from Day 32 to Day 57, and on Day 88, the cells contain many stage 5 neurons similar to the postnatal cranial nerves. This ability of transition of gene expression in human iPSC-derived neurons from the fetal brain to the postnatal brain state has so far been reported only in long-term 3D-cultured brain organoids for 250 days or longer (Gordon A., et al., Long-term maturation of human cortical organoids matches key early postnatal transitions, Nat. Neurosci. 24, 331-342, 2021). However, there have been no reports of a successful transition to the postnatal brain state in a relatively short period of time (57 to 88 days) in planar culture or simple spheroid culture composed only of nerve cells, and the difficulty thereof was suggested. In addition, culture conditions of brain organoids are complex, and spines and postsynaptic structures described later are not visualizable and quantifiable because of a configuration of containing a plurality of types of cells and aggregation of cells. Therefore, in the drug discovery screening and the like, there is a need for a method for producing mature neurons that are more suitable for practical use.

Experimental Example 3

(RNA-Seq Analysis 2)

An expression profile of known neuron-specific markers was examined based on the RNA-Seq data acquired in Experimental Example 2.

Figure 7:
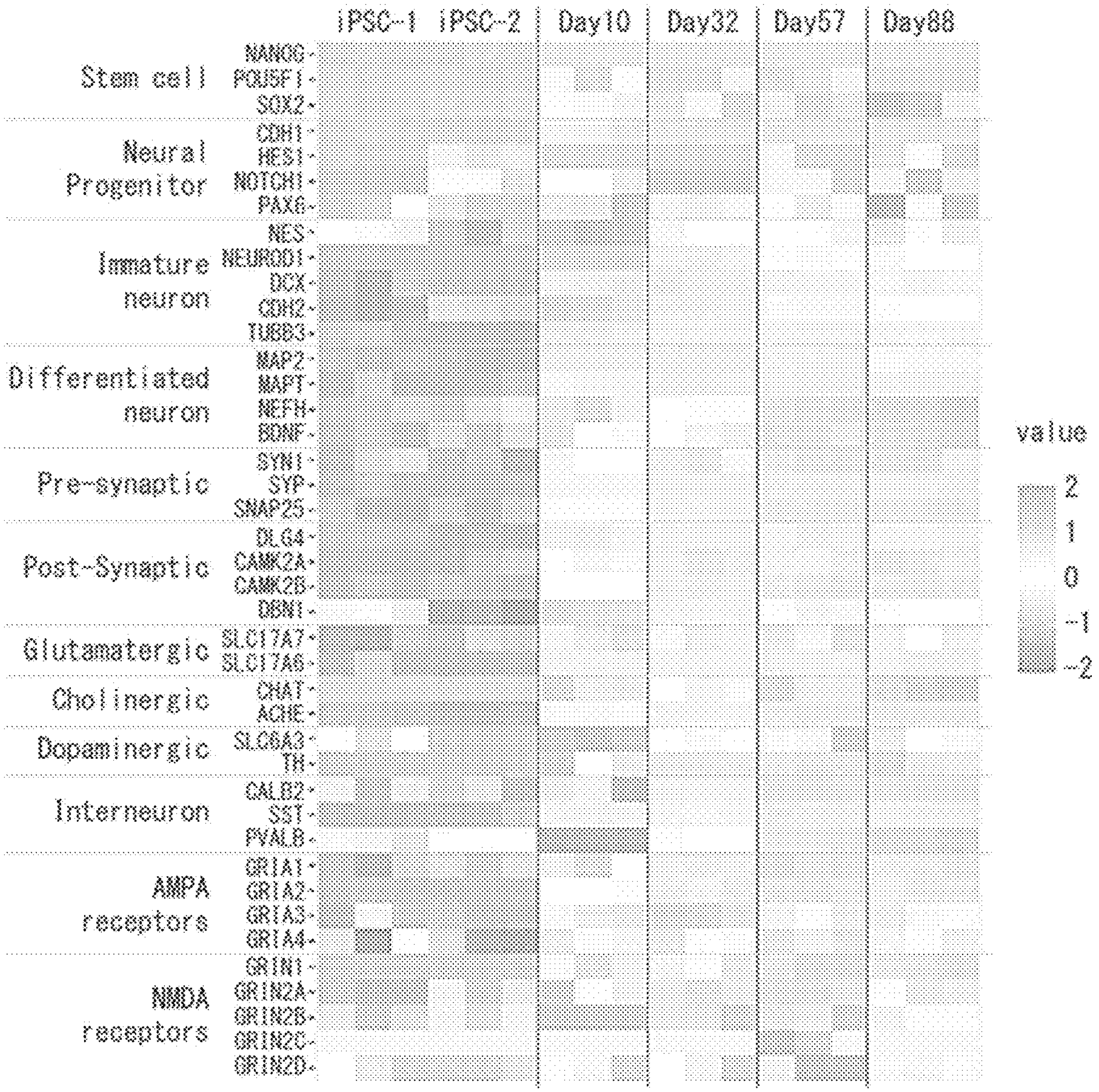
FIG. 7 is a heat map of an RNA-Seq expression profile in Experiential Example 3.

FIG. 7 is a heat map of the RNA-Seq expression profile. FIG. 7 shows the expression of major undifferentiated markers and neuron-specific markers. As a result, the time-dependent regulation of a transcriptional program was confirmed. Specifically, it was found that stem cell markers and proliferation markers were down-regulated on Day 10, and most cells were efficiently differentiated.

The neurons on Day 10 expressed neural progenitor cell markers (PAX6, NES, and other markers) and some neuronal marker, (NEUROD1, CDH2, TUBB3, MAP2, MAPT, and other markers). This result showed that the neurons were at the immature neuronal stage.

Subsequently, the expression of most neural progenitor cell markers and immature neuronal markers decreased. In contrast, increases in mature neuronal markers (NEPH, BDNF), presynaptic markers (SYN1, SYP, and SNAP25) and postsynaptic markers (DLG4 and CAMK2) were observed after Day 32.

It was also observed that glutamate vesicle transporters (SLC17A6 and SLC17A7), and AMPA receptors (GR1A1-4) were up-regulated, and subsequently NMDA receptors (GRIN1, -2A, and -2B) were up-regulated, which indicates that glutamatergic neurons capable of excitatory transmission were present.

Experimental Example 4

(RNA-Seq Analysis 3)

Based on the RNA-Seq data acquired in Experimental Example 2, genes were grouped by hierarchical clustering analysis of the expression profile, and gene ontology (GO) enrichment analysis was performed.

Figure 8:
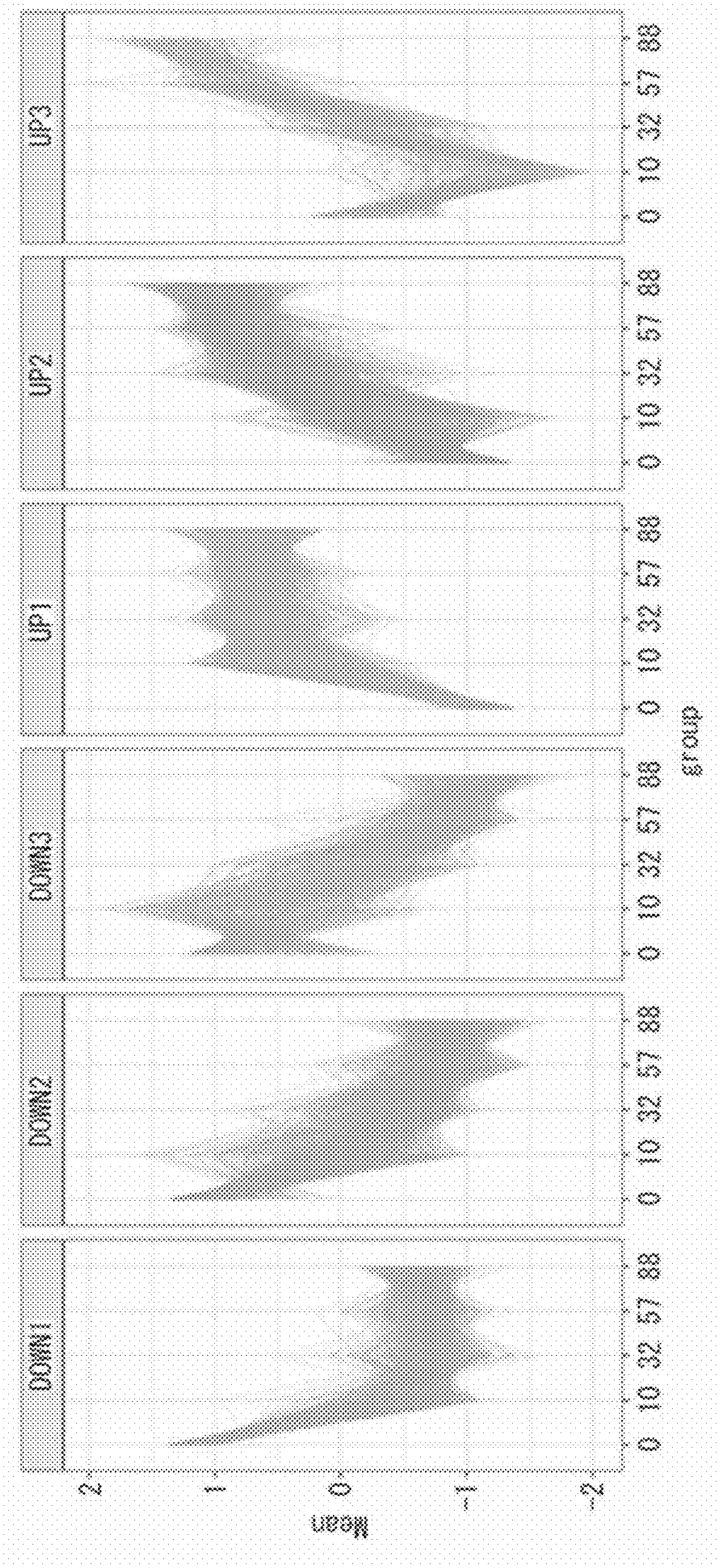
FIG. 8 is a graph showing the result of classifying a gene expression profile into six patterns in Experimental Example 4.

FIG. 8 is a graph showing the result of classifying the gene expression profile into six patterns based on the average expression level of individual genes on Day 0, Day 10, Day 32, Day 57, and Day 88.

Figure 9A:
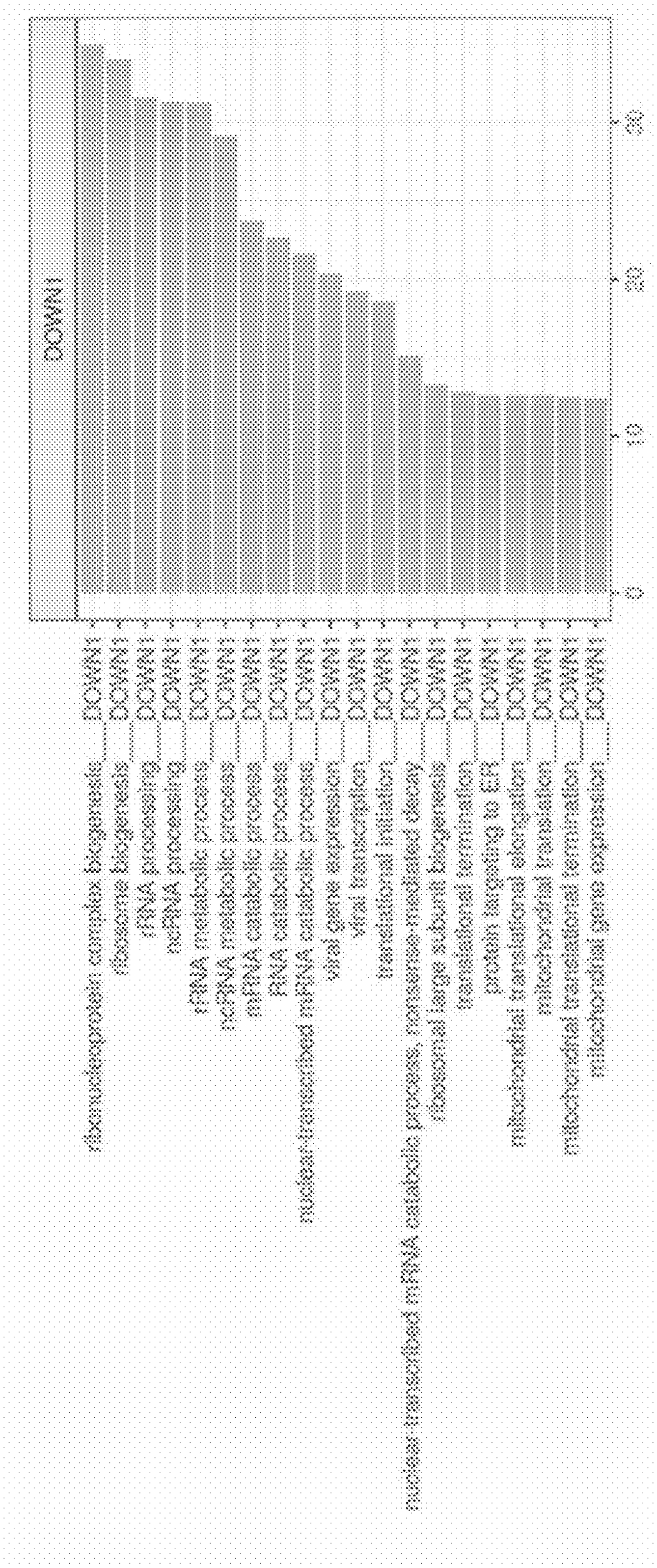
FIG. 9A is a graph showing the top 20 significantly enriched gene ontology terms for a cluster DOWN1 in Experimental Example 4.
Figure 9B:
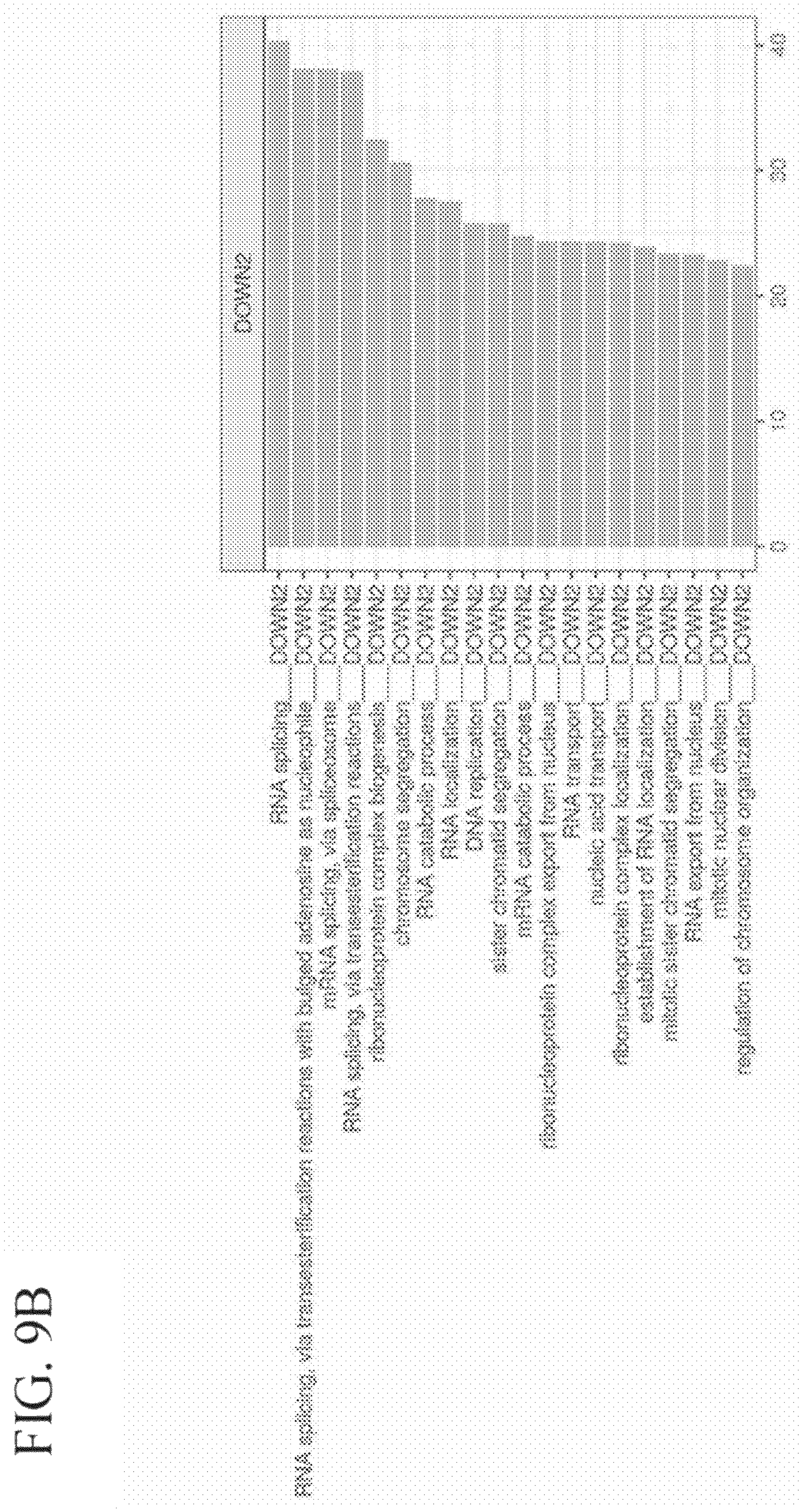
FIG. 9C is a graph showing the top 20 significantly enriched gene ontology terms for a cluster DOWN3 in Experimental Example 4.
Figure 9C:
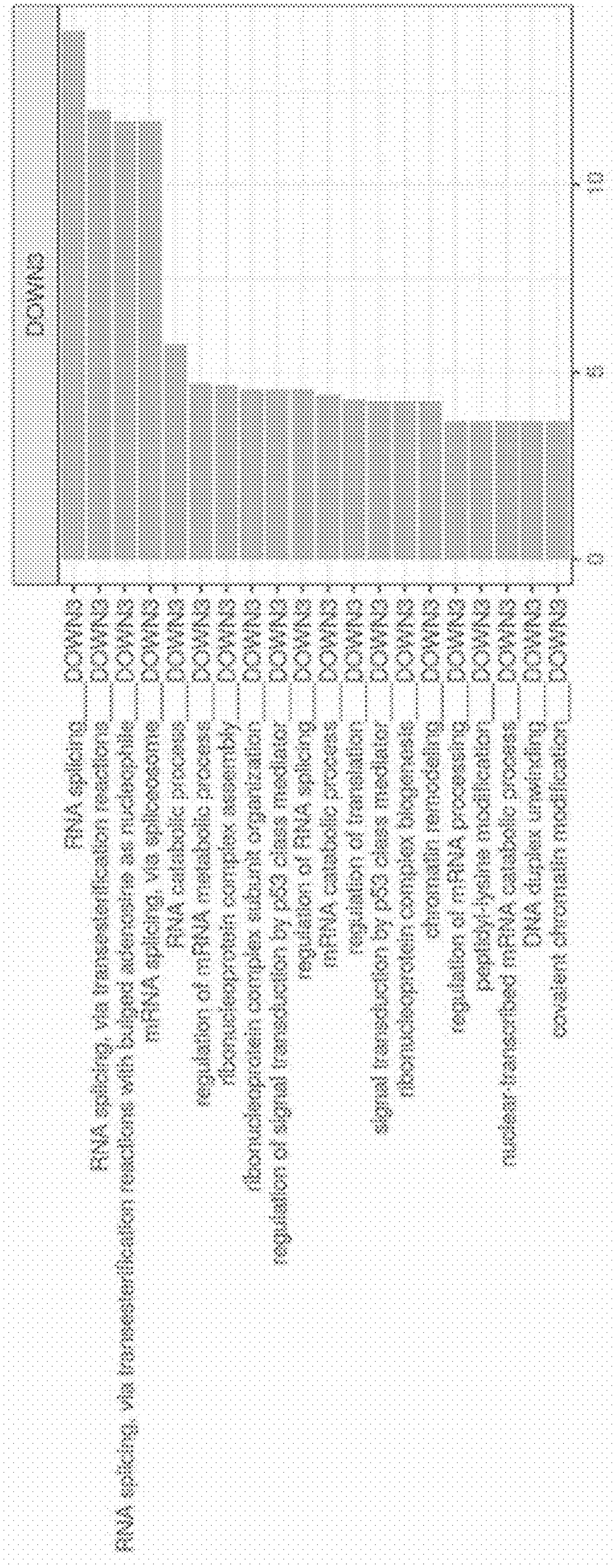

FIGS. 9A, 9B, and 9C are graphs showing the top 20 significantly enriched gene ontology terms for clusters DOWN1, DOWN2, and DOWN3, respectively.

Figure 10A:
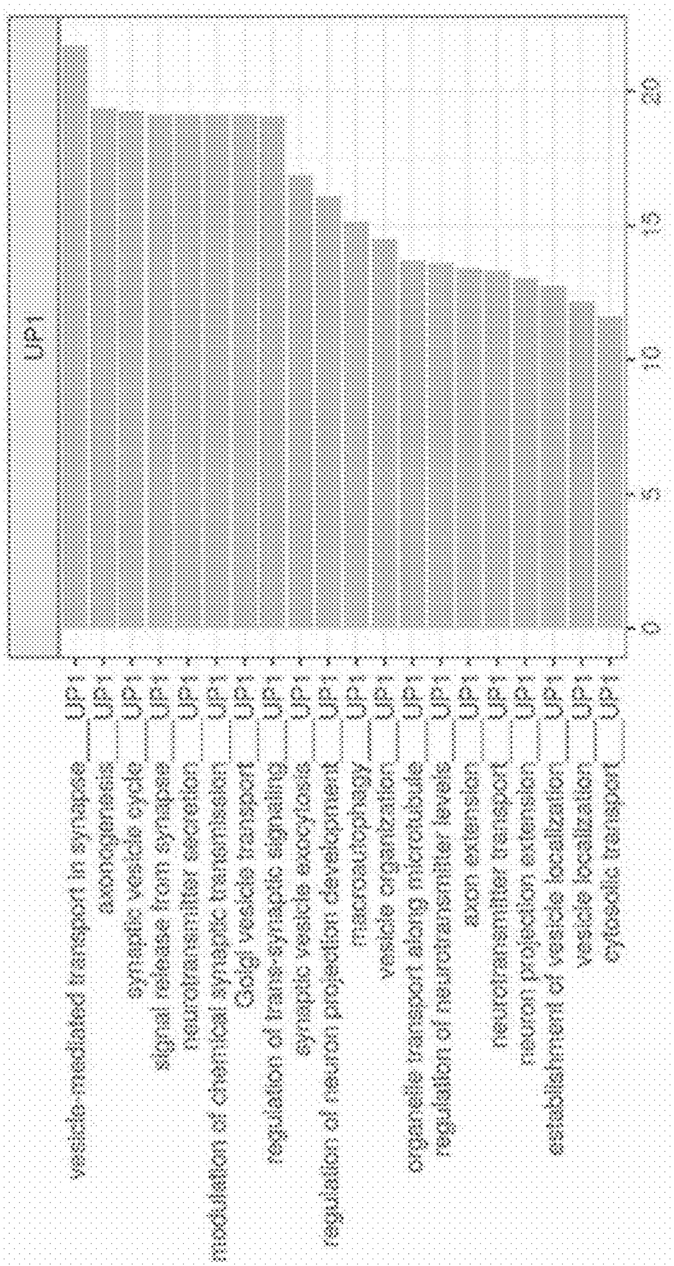
FIG. 10A is a graph showing the top 20 significantly enriched gene ontology terms for a cluster UP1 in Experimental Example 4.
Figure 10B:
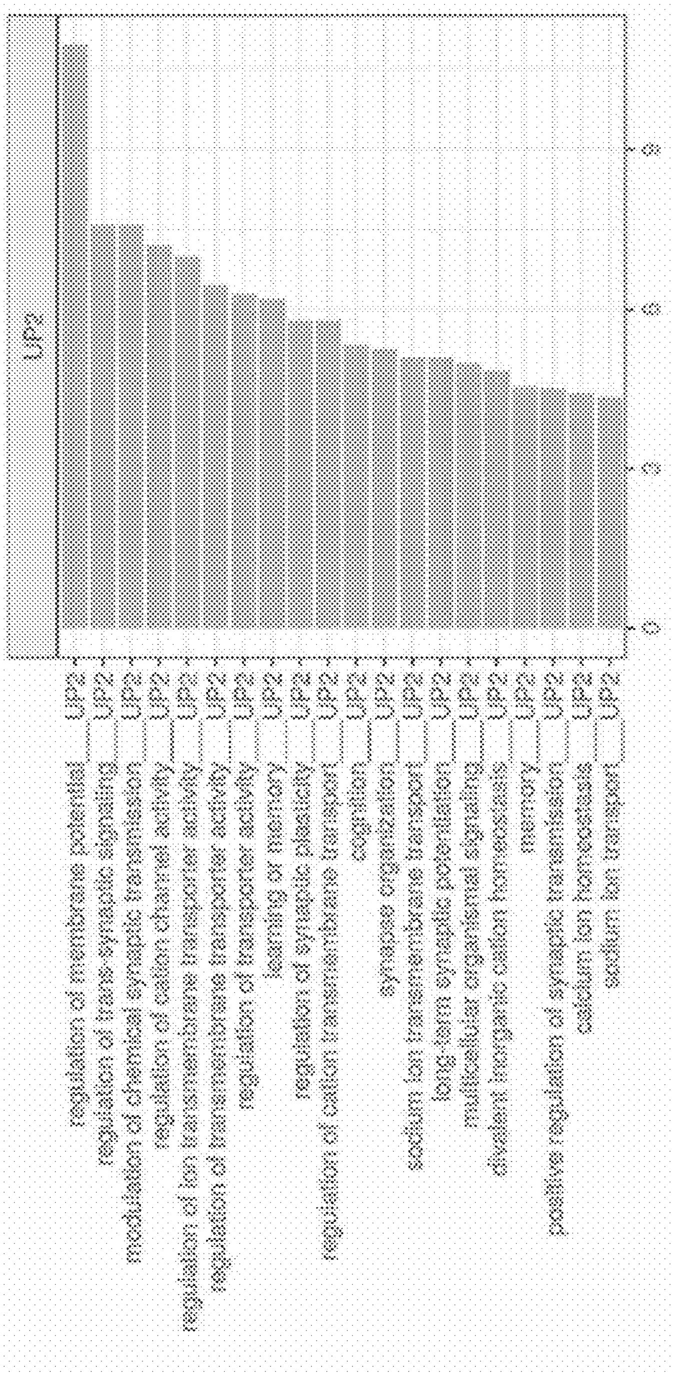
FIG. 10B is a graph showing the top 20 significantly enriched gene ontology terms for a cluster UP2 in Experimental Example 4.
Figure 10C:
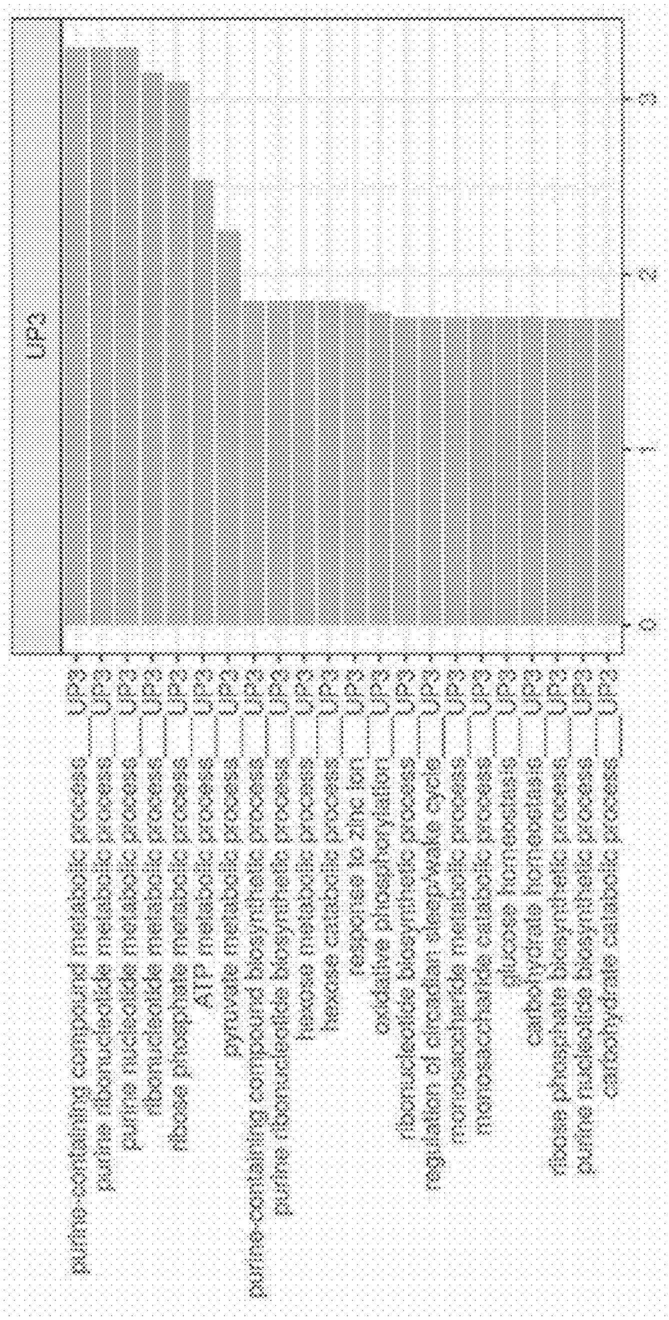

FIGS. 10A, 108, and 10C are graphs showing the top 20 significantly enriched gene ontology terms for clusters UP1, UP2, and UP3, respectively.

The results showed that genes (cluster UP1) that were immediately up-regulated on Day 10 were mainly associated with axonogenesis, neuronal projection, and formation and transport of presynaptic vesicles, which indicated active neuronal development.

In contrast, genes that were strongly up-regulated after Day 32 (cluster UP2) were involved in the regulation of functions that require more mature postsynaptic structures (learning or memory, plasticity, long-term potentiation), transmembrane ion transport, and synaptic functions. This suggested increased synaptogenesis and neurotransmission activity in late time points.

It was considered that cluster UP3 was enriched in purine metabolism, oxidative phosphorylation, and respiratory function in order to satisfy the high demand for ATP synthesis in neurogenesis and neurotransmission.

The down-regulated clusters were mostly enriched for RNA processing and splicing functions, which reflected dramatic translational changes required to achieve complex cell differentiation. The cluster DOWN2 contained genes associated with nuclear division and chromosome/chromatid segregation, and possibly associated with cell cycle exit in differentiated neurons.

These results of RNA-Seq analyses suggested that following early induction of differentiation, specific long-term transcriptional programs regulate neuronal maturation and synaptogenesis.

Experimental Example 5

(Examination 1 by Immunostaining)

Human iPSC-derived neurons (product name "Quick-Neuron (trademark) Excitatory-Human iPSC-derived Neurons", ELIXIRGEN SCIENTIFIC, INC.), which were cultured in the sane manner as in Experimental Example 1, were immunostained, and the growth of neurites and the formation of synaptic structures were observed.

Figure 11:
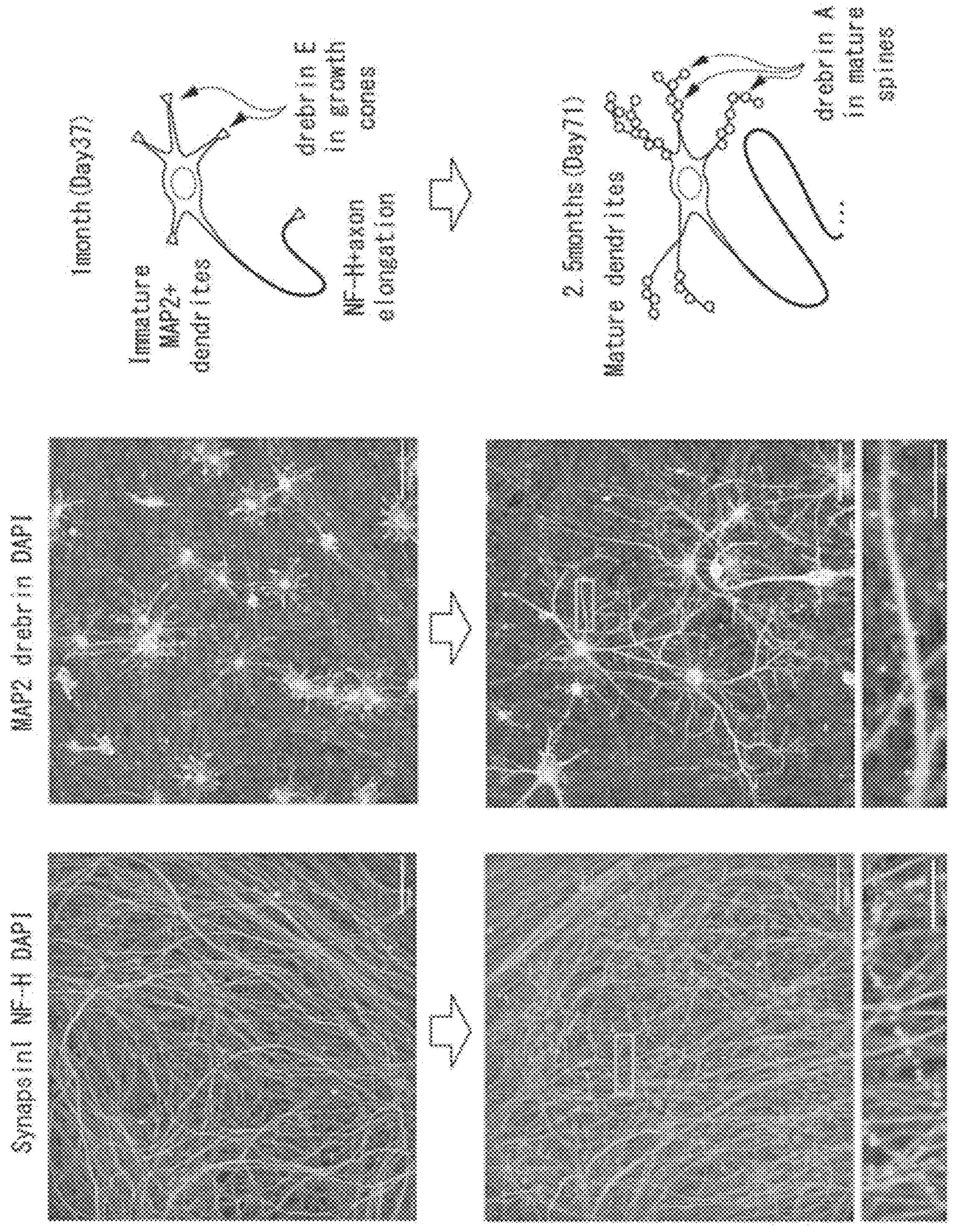
FIG. 11 shows representative fluorescence microscope images representing the results of immunostaining in Experimental Example 5.

FIG. 11 shows fluorescence microscope images representing the representative results of immunostaining the neurons on Day 37 and Day 71. Enlarged images of areas surrounded by squares in the image of Day 71 in the middle are shown in the lower side. The upper side scale bar is 100 μm and the lower side scale bar is 20 μm. In FIG. 11, staining results of neurofilament heavy chain (NF-H) serving as an axonal marker, and synapsin I serving as a presynaptic marker are shown on the left, staining results of MAP2 serving as a dendrite marker, and drebrin serving as a postsynaptic marker are shown in the center, and schematic diagrams for interpreting a state of each neuron are shown on the right.

iPSC-derived neurons developed short MAP2-positive dendrites and neurofilament heavy chain (NF-H)-positive axons, which rapidly elongate, one month after initiation of culture. As in Example 1, the MAP2-positive dendrites continued to grow and branch over time.

In association with this, an increase in the expression of synapsin I serving as the presynaptic marker was accompanied. The synapsin I diffused around axons and cell bodies in the early culture and aggregated along mature dendrites in later culture on Day 71. It was indicated that synapsin I concentrates at synaptic sites as neuronal development proceeds from stage 4 onwards.

Intracellular localization of drebrin, which is an actin-binding protein, was subsequently assessed. In early culture from culture initiation to Day 37, drebrin was distributed around a cell body and in a growth cone at the end of developing a dendrite. On Day 71, drebrin clustered along mature MAP2-positive dendrites.

Experimental Example 6

(Examination 2 by Immunostaining)

A neural cell differentiation kit (product name: "Quick-Neuron (trademark) Excitatory-SeV Kit", ELIXIRGEN SCIENTIFIC, INC.) was used to prepare stage 3 neurons from healthy subject-derived iPSCs according to the manufacturer's protocol. The 1231A3 strain was used as the healthy subject-derived iPSCs. Reproducibility of maturation was confirmed by using strains different from Experimental Example 1, and immunostaining images with higher resolution were obtained.

Figure 12:
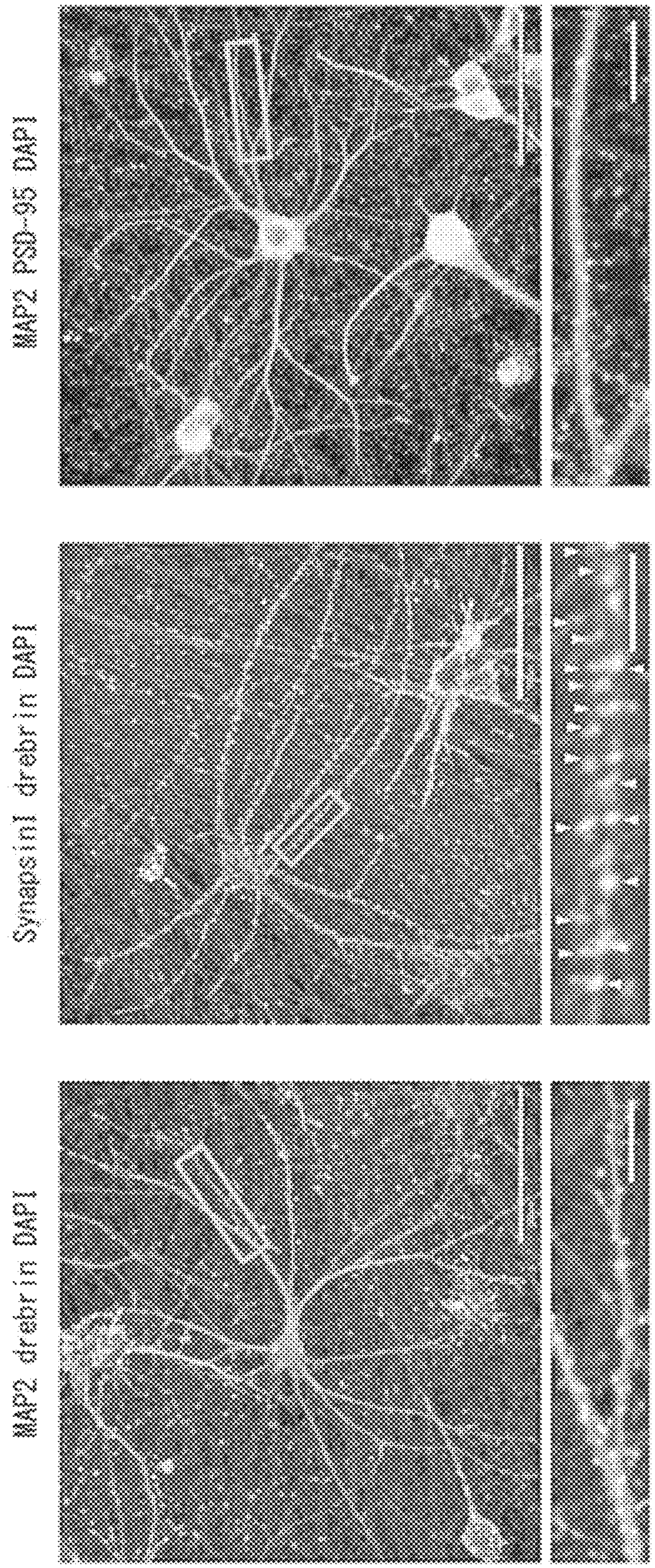
FIG. 12 shows representative fluorescence microscope images representing the results of immunostaining in Experimental Example 6.

FIG. 12 shows fluorescence microscope images representing the representative results of immunostaining the iPSC-derived neurons on Day 73. Enlarged images of areas surrounded by squares at the upper side are shown at the lower side. The upper side scale bar is 100 μm and the lower side scale bar is 10 μm.

As a result, expression of Postsynaptic density protein 95 (PSD95) was also observed. It was also found that synapsin I of the presynaptic marker, drebrin of the postsynaptic marker, and PSD95 formed clusters on or near dendrites.

In addition, in the center figure of FIG. 12, it was found that clusters of synapsin I and drebrin were adjacent to each other or partially co-localized (white arrows), and in the dendritic spines, presynapse and postsynapses were connected to establish synaptic connections.

The above-described result indicates that the iPSC-derived neurons matured into stage 5 neurons with mature dendrites. That is, it was shown that stage 5 neurons could be produced by culturing stage 3 neurons in the culture medium containing B-27 Plus.

Experimental Example 7

(Examination 3 by Immunostaining)

Human iPSC-derived neurons (product name "Quick-Neuron (trademark) Excitatory-Human iPSC-derived Neurons", ELIXIRGEN SCIENTIFIC, INC.), which were cultured in the same manner as in Experimental Example 1, were immunostained, and the expression of known neuron-specific markers was observed. Nuclei were also stained with DAPI.

Figure 13:
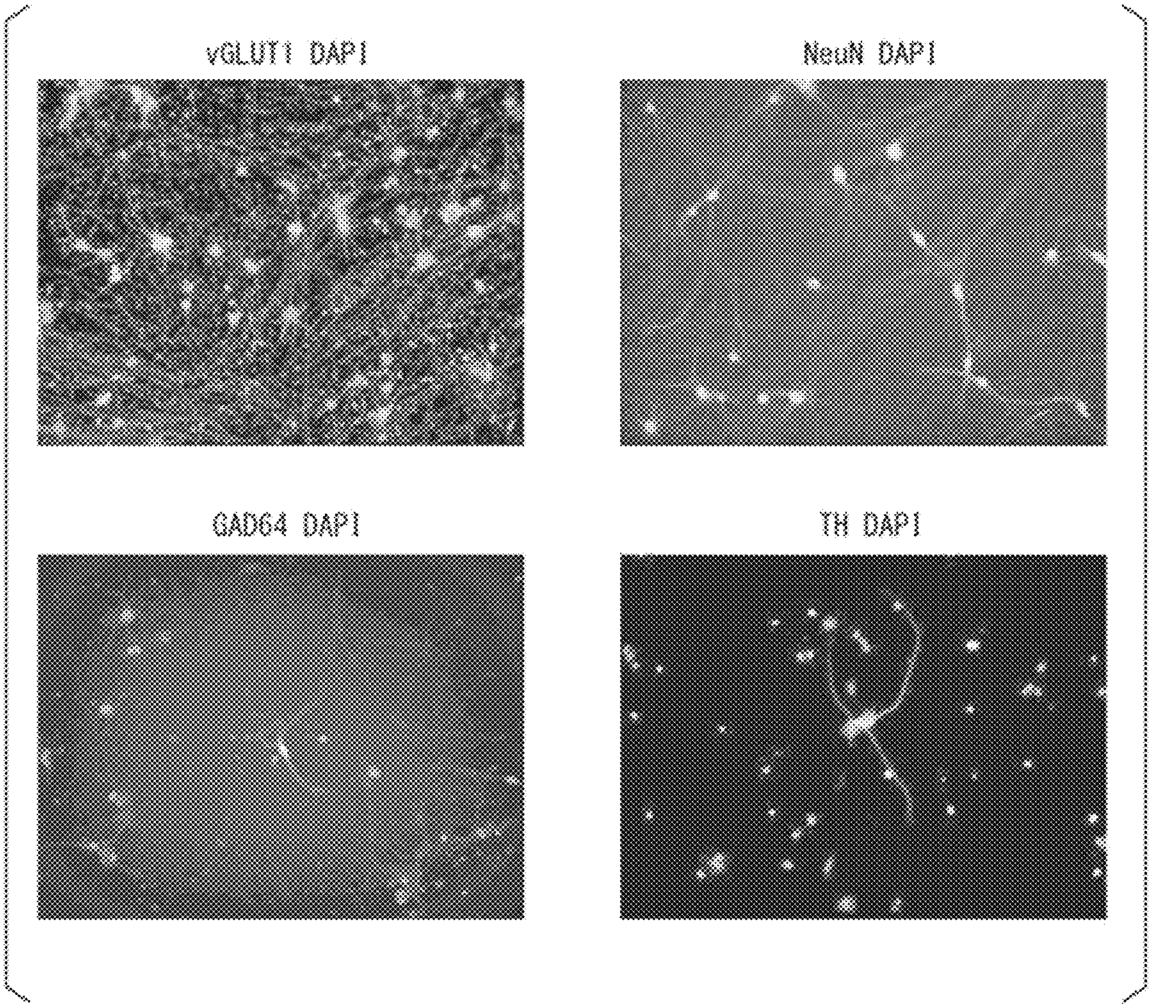
FIG. 13 shows representative fluorescence microscope images representing the results of immunostaining in Experimental Example 7.

FIG. 13 shows fluorescence microscope images representing the representative results of immunostaining the iPSC-derived neurons. Scale bar is 100 μm. As a result, it was confirmed that most (95% or more) cells expressed vGLUT1 serving as the glutamatergic neuronal marker on Day 28 and expressed NeuN serving as the mature neuronal marker on Day 85. It was also confirmed that some cells (5% or less) expressed GAD64 serving as a GABAergic neuronal marker, and TH serving as a dopaminergic neuronal marker on Day 85.

Experimental Example 8

(Examination of Drebrin Isoforms)

It is known that changes in the intracellular localization of drebrin during neuronal development are caused by alternative splicing of drebrin. Drebrin E with the embryonic isoform plays a role in immature neuronal migration and neurite growth, and is replaced by drebrin A, which is a mature brain-specific adult-type isoform and regulates the formation of dendritic spines and plasticity accompanied by maturation of neurons.

Figure 14:
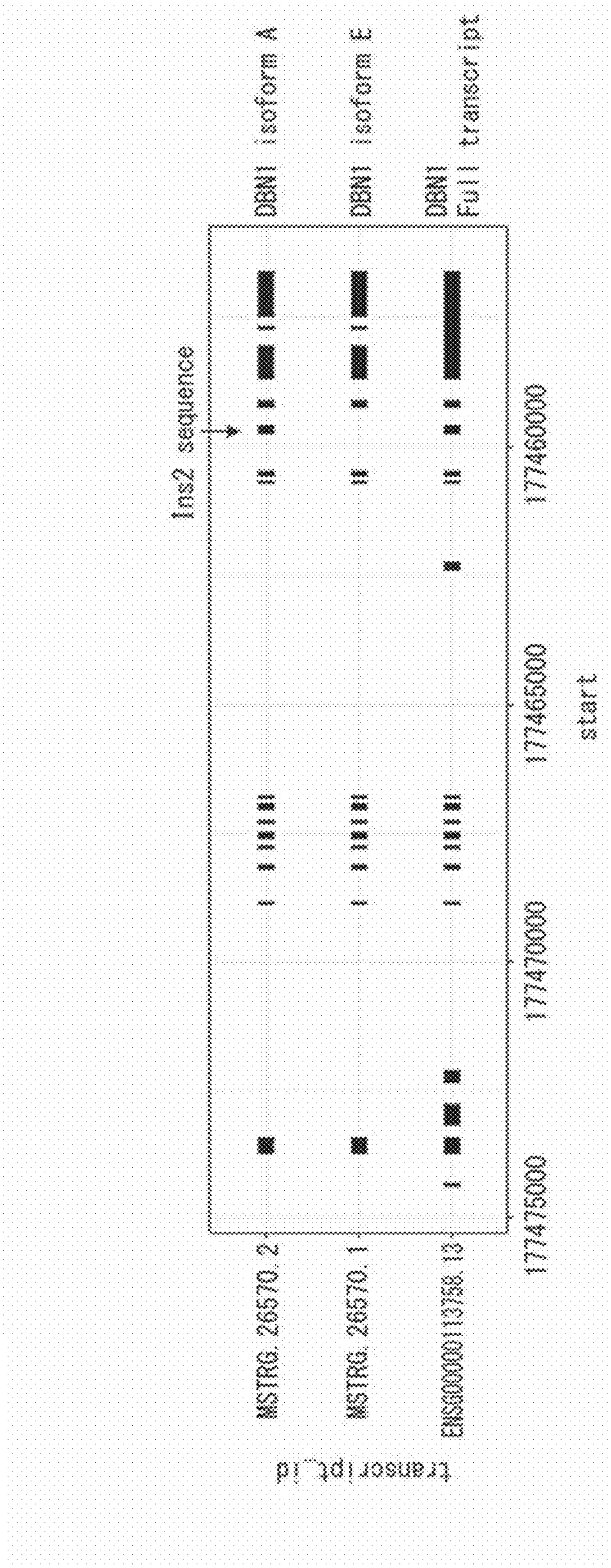
FIG. 14 is a diagram showing base sequences of two drebrin isoforms identified by mapping RNA-Seq data to the DBN1 locus of the human reference genome in Experimental Example 8.

FIG. 14 is a diagram showing the base sequences of two drebrin isoforms identified by mapping RNA-Seq data to the DBN1 locus of the human reference genome.

A transcript containing additional exon 11 was assumed to be the mature brain-specific adult isoform A, and a shorter transcript was assumed to be the embryonic isoform E.

Figure 15:
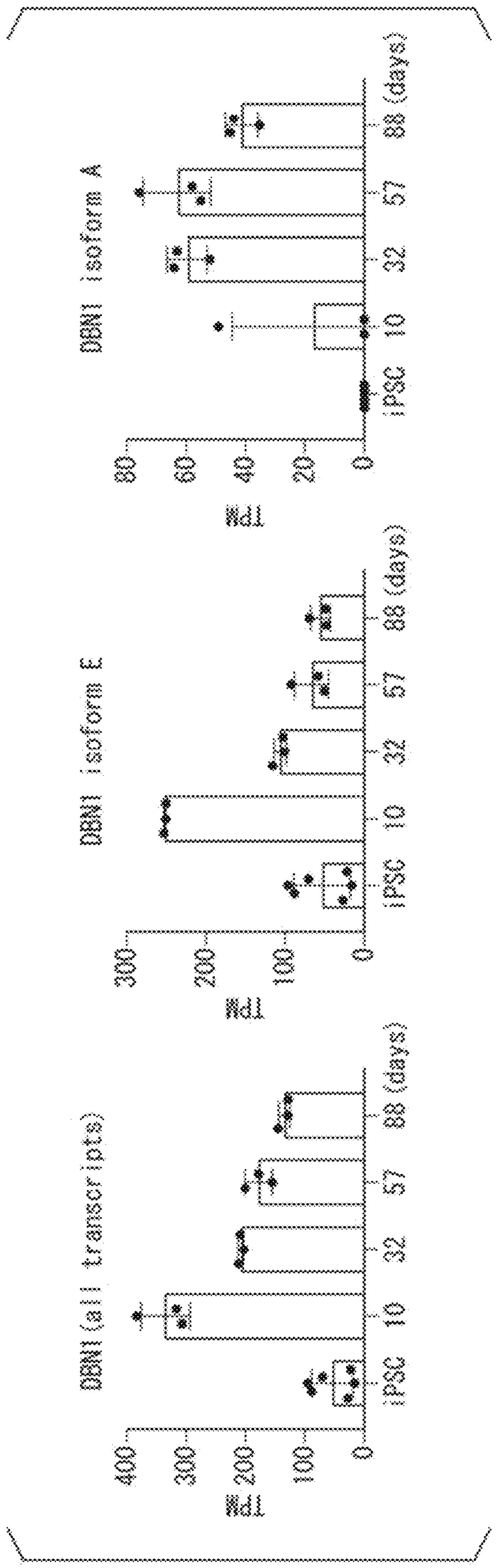
FIG. 15 is a graph showing expression levels of the drebrin isoforms detected by analysis of RNA-Seq data in Experimental Example 8.

Based on the RNA-Seq data acquired in Experimental Example 2, the expression levels of drebrin isoforms were analyzed. FIG. 15 is a graph showing expression levels (transcripts per million, TPM) of all transcripts in drebrin and each isoform detected by analysis of the RNA-Seq data.

As a result, it was shown that drebrin (total) and the embryonic isoform E were expressed in undifferentiated iPSCs, up-regulated upon induction of differentiation, and down-regulated again in later time points. The adult isoforms A was almost not present in the early stage of differentiation and induced to be expressed in the later stage.

Figure 16:
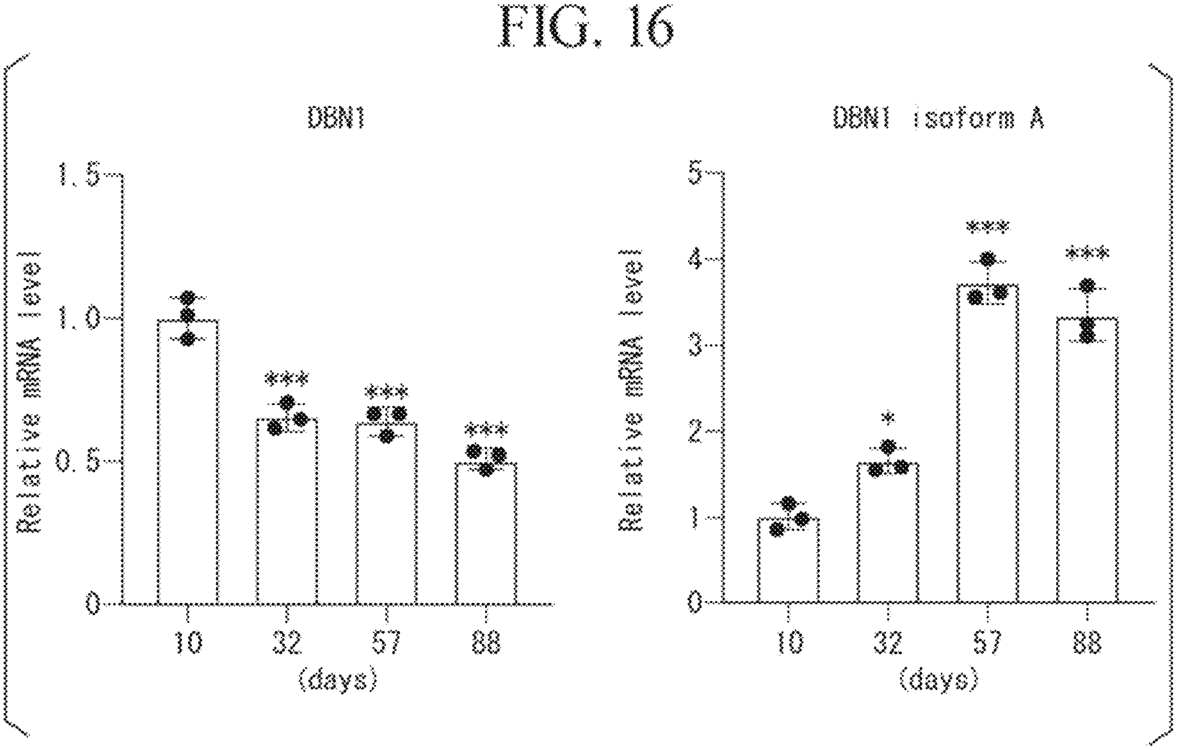
FIG. 16 is a graph showing the result of analyzing expression levels of drebrin (total) and drebrin isoform A by quantitative real-time RT-PCR in Experimental Example 8.

FIG. 16 is a graph showing the result of analyzing expression levels of drebrin (total) and drebrin isoform A by quantitative real-time RT-PCR on human iPSC-derived neurons cultured in the same manner as in Experimental Example 1. In FIG. 16, "DBN1" represents the expression level of drebrin (total), "DBN1 isoform A" represents the expression level of drebrin isoform A, "*" represents a significant difference at $p<0.05$, and "**" represents a significant difference at $p<0.001$. As a result, it was confirmed that the isoform A was up-regulated particularly after Day 57.

According to the above-described result, the maturation of iPSC-derived neurons appeared to recapitulate the molecular event of drebrin isoform switching previously known in rodent hippocampal neurons.

Experimental Example 9

(Examination of Subunit of NMDA Receptor)

Figure 17:
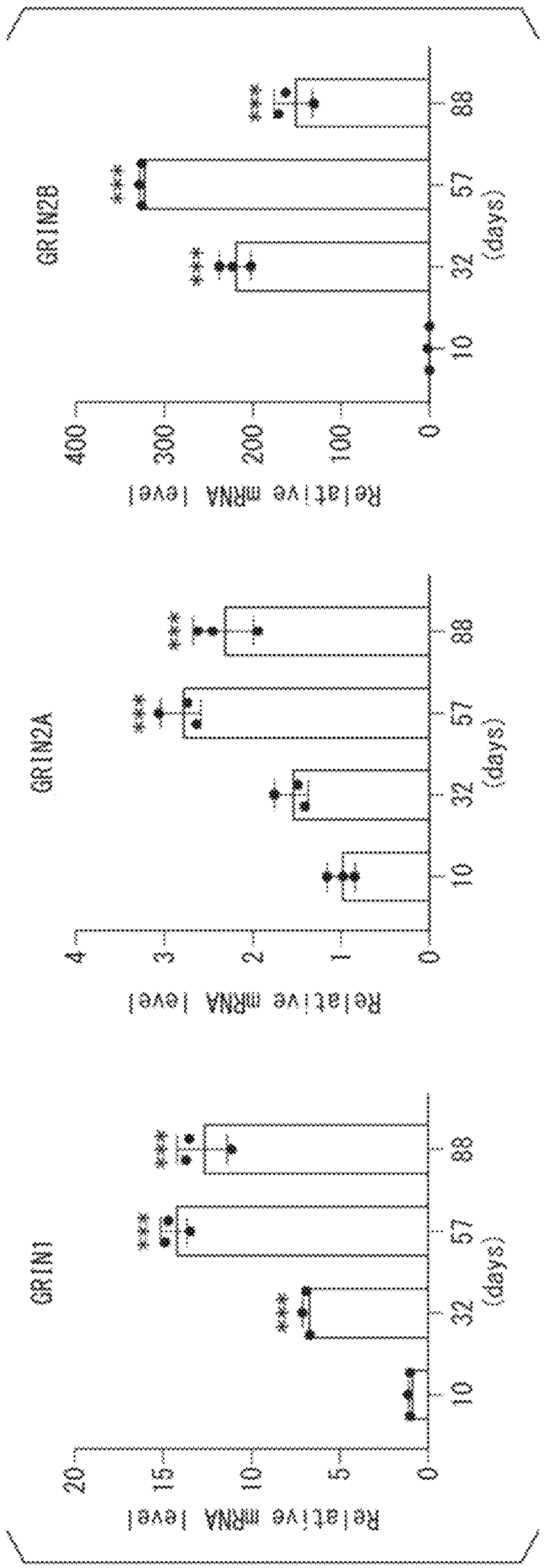
FIG. 17 is a graph showing the result of measuring relative expression levels of GRIN1, GRIN2A, and GRIN2B, which are subunits of an NMDA receptor, by quantitative real-time RT-PCR in Experimental Example 9.

It is known that properties of the NMDA receptor change during maturation, resulting in a developmental switch from the subunit GluN2B (GRIN2B) to the subunit GluN2A (GRIN2A), FIG. 17 is a graph showing the result of measuring relative expression levels of GRIN1, GRIN2A, and GRIN2B, which are subunits of an NMDA receptor, by quantitative real-time RT-PCR on human iPSC-derived neurons cultured in the same manner as in Experimental Example 1. In FIG. 17, "***" represents that there is a significant difference at $p<0.001$ with respect to the result of Day 10, and "###" represents that there is a significant difference at $p<0.001$ with respect to the result of GRIN2B on Day 57.

As a result, it was shown that GRIN1 and GRIN2B were significantly up-regulated on Day 32, and GRIN2A was significantly up-regulated on Day 57, GRIN2B was also significantly down-regulated again on Day 88, and it was found that a developmental switch from GluN2B to GluN2A was induced.

Experimental Example 10

(Examination of Tau Isoforms)

It is known that tau (gene name: MAPT), which stabilizes microtubules in nerve cells, expresses six isoforms by alternative splicing, three of which have three repeat sequences (3R tau isoforms), and three others have four repeat sequences (4R tau isoforms), thereby distinguishable from each other. It is known that only 3R tau is expressed in the embryonic period, but the number of isoforms to be expressed increases with maturity, and 4R tau is expressed in the brain of a living body.

Figure 18:
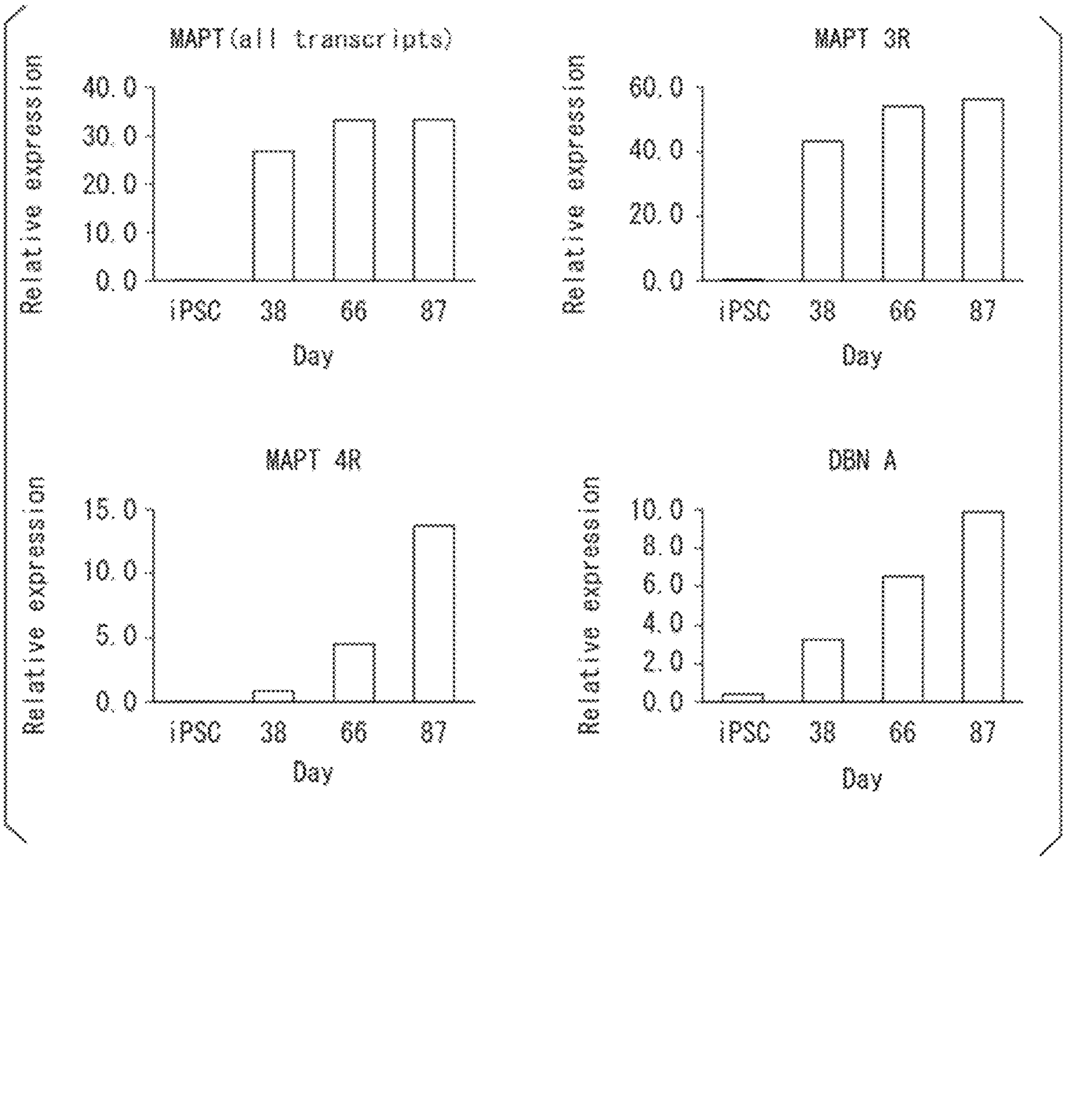
FIG. 18 is a graph showing the result or measuring relative expression levels of tau (total), 3R tau isoform, 4R tau isoform, and drebrin isoform A by quantitative real-time RT-PCR in Experimental Example 10.

FIG. 18 is a graph showing the results of relative expression levels of tau total), 3R tau, 4R tau, and drebrin isoform A measured by quantitative real-time RT-PCR in human iPSC-derived neurons cultured in the same manner as in Experimental Example 1. As a result, it was shown that tau (total) and 3R tau were highly expressed from Day 38, whereas 4R tau was up-regulated on Day 66 and Day 87, similar to the drebrin isoform A.

Experimental Example 11

(Examination 1 of Functional Activity of Excitatory Postsynaptic Protein)

Electrophysiological responses of the human iPSC-derived neurons were analyzed by using a high-density microelectrode array system (HD-MEA, MaxWell Biosystems AG).

Human iPSC-derived neurons (product name "Quick-Neuron (trademark) Excitatory-Human iPSC-derived Neurons", ELIXIRGEN SCIENTIFIC, INC.) were cultured in the same manner as in Experimental Example 1, except that the human iPSC-derived neurons were seeded on electrodes of the high-density microelectrode array (HD-MEA) at a cell density of 100,000 cells/well, and the local electric field potential was measured over time.

Figure 19:
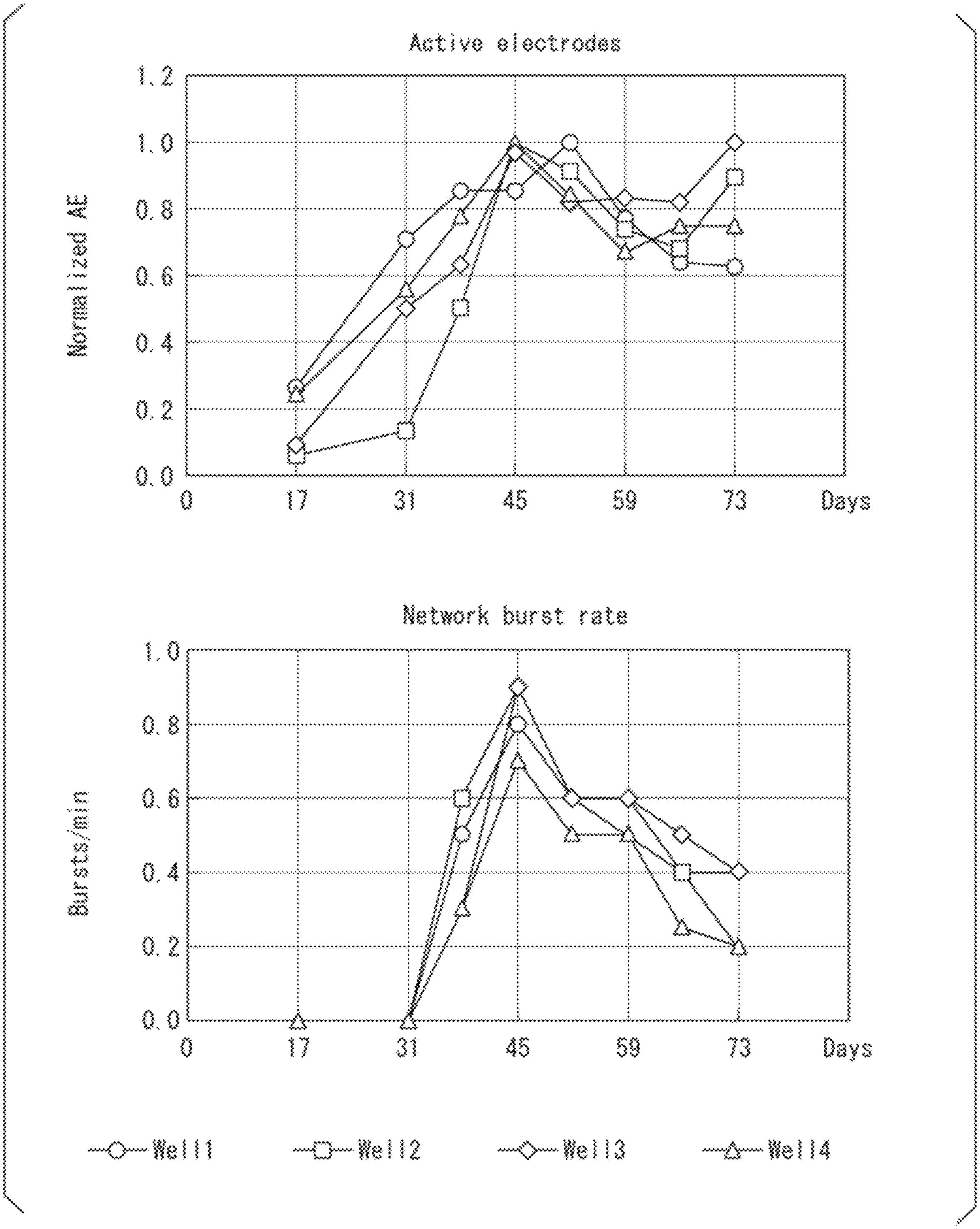
FIG. 19 is a graph showing the number of electrical activity detection electrodes and the synchronized network burst frequency of iPSC-derived neurons measured in Experimental Example 11.

FIG. 19 is a graph showing the number of electrical activity detection electrodes (active electrodes) and synchronized network burst frequency (network burst rate) measured in four independent wells of the cultured iPSC-derived neurons over time. The number of electrical activity detection electrodes is proportional to the presence of spontaneously firing cells and is an indicator of firing activity. Synchronized network burst is an indicator of the establishment of connections between cultured neurons.

As a result, it was shown that the firing activity increased after Day 31, and reproducible network bursts appeared. The network bursts were stably measured until about 8 weeks after the initiation of culture, and then decreased again with maturity. It was considered that it is not due to a decrease in the electrical activity itself or viability of individual cells, but due to replacement with chemical synapses that enable more selective control from electrical synapses via gap junctions that do not require maturation of inhibitory neurons or postsynaptic functions because no decrease in firing activity was observed.

4-Aminopyridine (4-AP) serving as a potassium channel inhibitor and D-2-Amino-5-phosphonopentanoic acid (D-AP5) serving ax an NMDA receptor inhibitor were added in the culture medium of iPSC-derived neurons at 8 weeks after the initiation of culture while increasing each concentration, and population firing rate histograms were recorded with 1,024 electrodes per well. One-minute stabilization and 10-minute recording were performed for each concentration. Finally, the iPSC-derived neurons were washed with three medium replacements and left for one day, and it was confirmed that the effect of each drug had disappeared.

Figure 20:
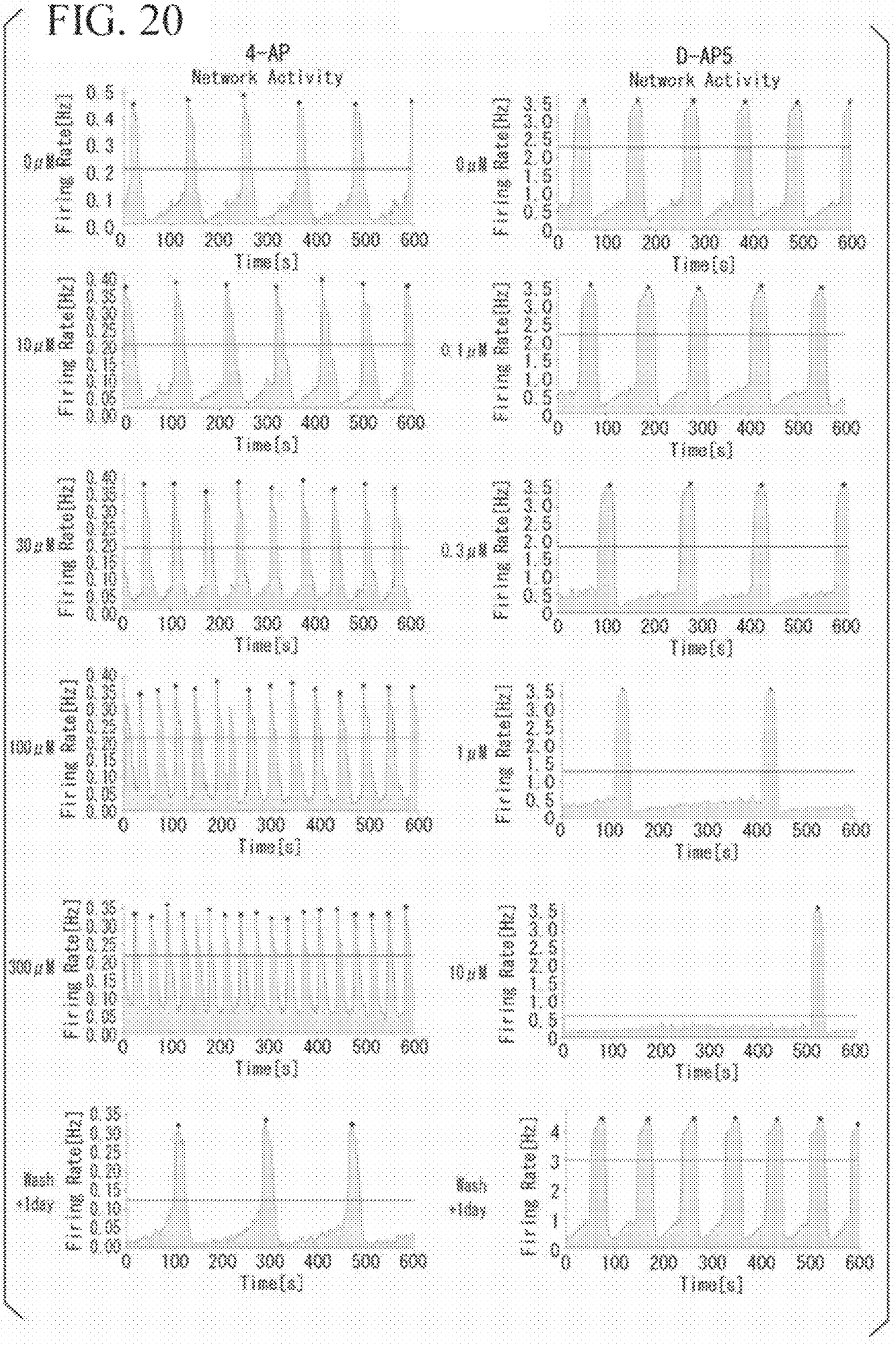
FIG. 20 is a graph showing a representative population firing rate histogram measured in Experimental Example 11.
Figure 21:
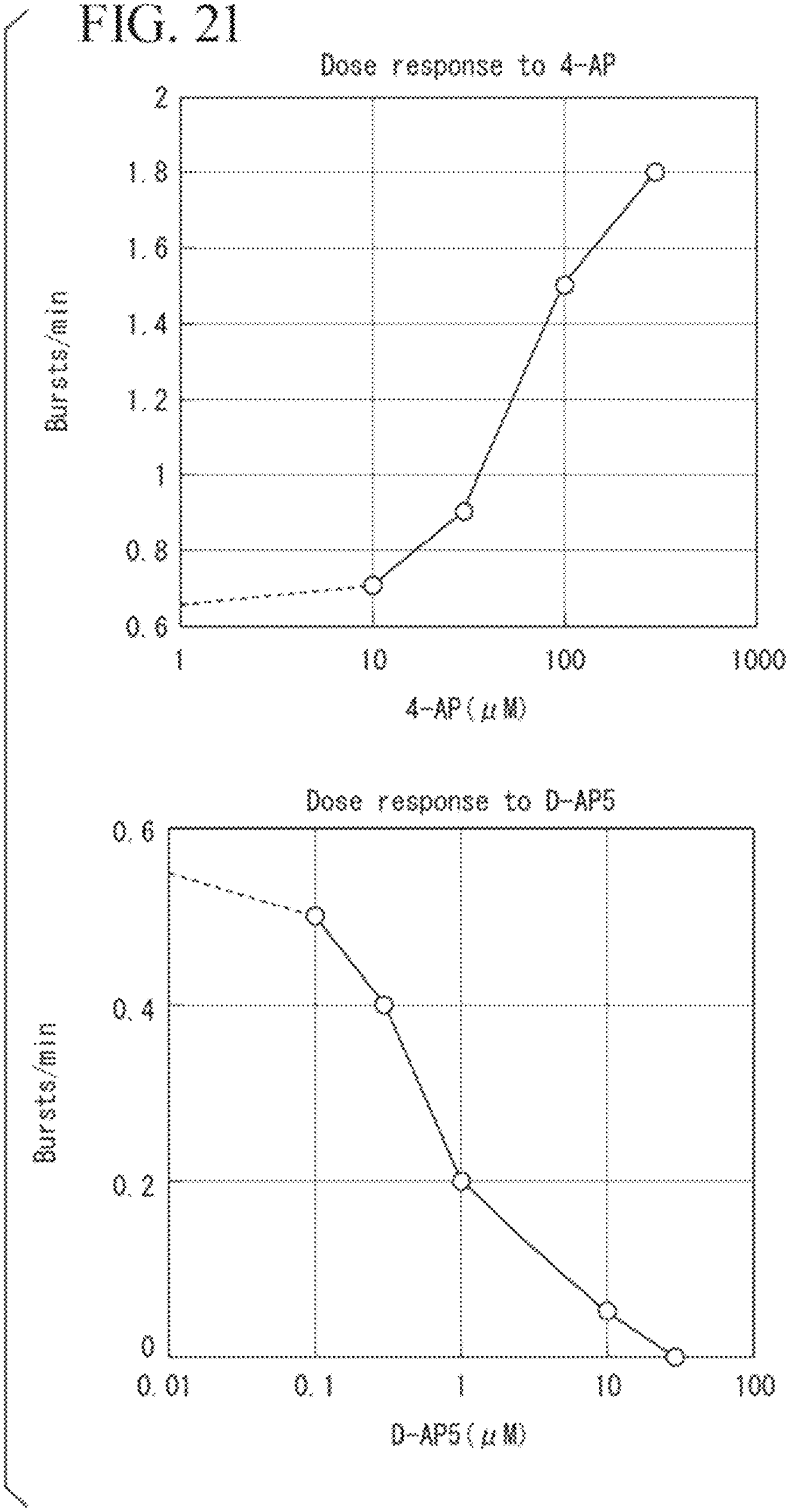
FIG. 21 is a dose response curve for 4-AP and D-AP5 prepared based on FIG. 20.

FIG. 20 is a graph showing a representative population firing rate histogram. FIG. 21 is a dose response curve for 4-AP and D-AP5 prepared based on FIG. 20. As a result, dose-dependent responses of iPSC-derived neurons to 4-AP and D-AP5 were observed. This result indicates that neurotransmission is functioning in the iPSC-derived neurons. It was found that synaptic transmission mediated by the NMDA receptors, which is particularly important in mature central nerves, functions.

Figure 22:
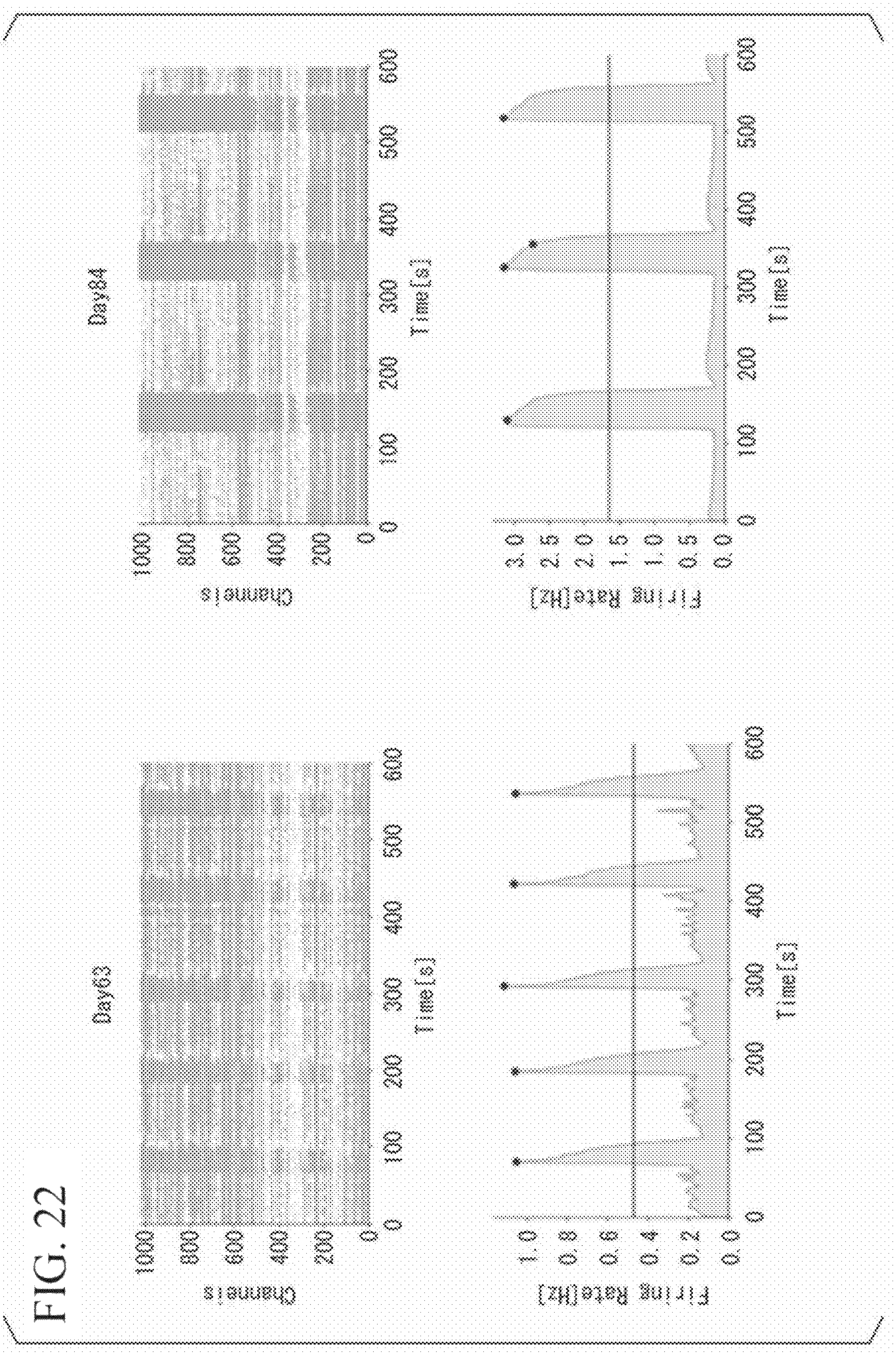
FIG. 22 is a raster plot of firing rates on Day 63 and Day 84 and representative population firing rate histograms showing network bursts, measured in Experimental Example 11.

FIG. 22 is a representative population firing rate histogram showing a raster plot of firing rates measured for 600 seconds using 1,024 electrodes and network bursts on Day 63 and Day 84. It was shown that a frequency of the network burst decreased on Day 84 compared to Day 63, while the burst duration, average firing rate within burst, and burst interval increased at the same time.

Figure 23:
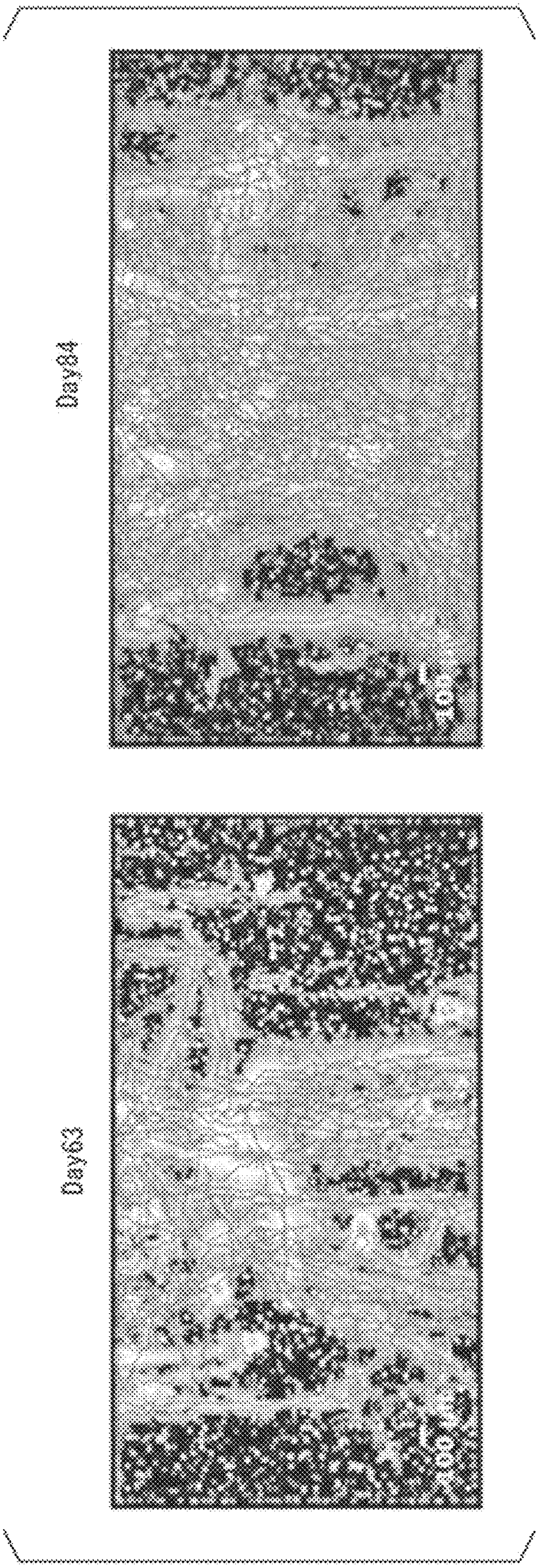
FIG. 23 is a graph showing a representative neurotransmission map in which the action potential propagation path is reconstructed on an electrode surface by an axon tracing assay on Day 63 and Day 84 in Experimental Example 11.

FIG. 23 is a graph showing a representative neurotransmission map in which the action potential propagation path was reconstructed on a 4 mm×2 mm area containing 26,400 electrodes by an axon tracing assay on Day 63 and Day 84. Scale bar is 100 μm. As a result, it was shown that the propagation distance of the action potential and the complexity of the network increased on Day 84 compared to Day 63. It was fond from these results that in the mature stage 5 neurons, the connectivity and stability of neural networks increased without abating electrical activity.

Experimental Example 12

(Examination 2 of Functional Activity of Excitatory Postsynaptic Protein)

Human iPSC-derived mature stage 5 neurons were treated with 100 μM glutamic acid for 10 minutes and then immunostained to examine the localization change of drebrin. For comparison, a sample immunostained without glutamic acid treatment was also prepared.

Figure 24:
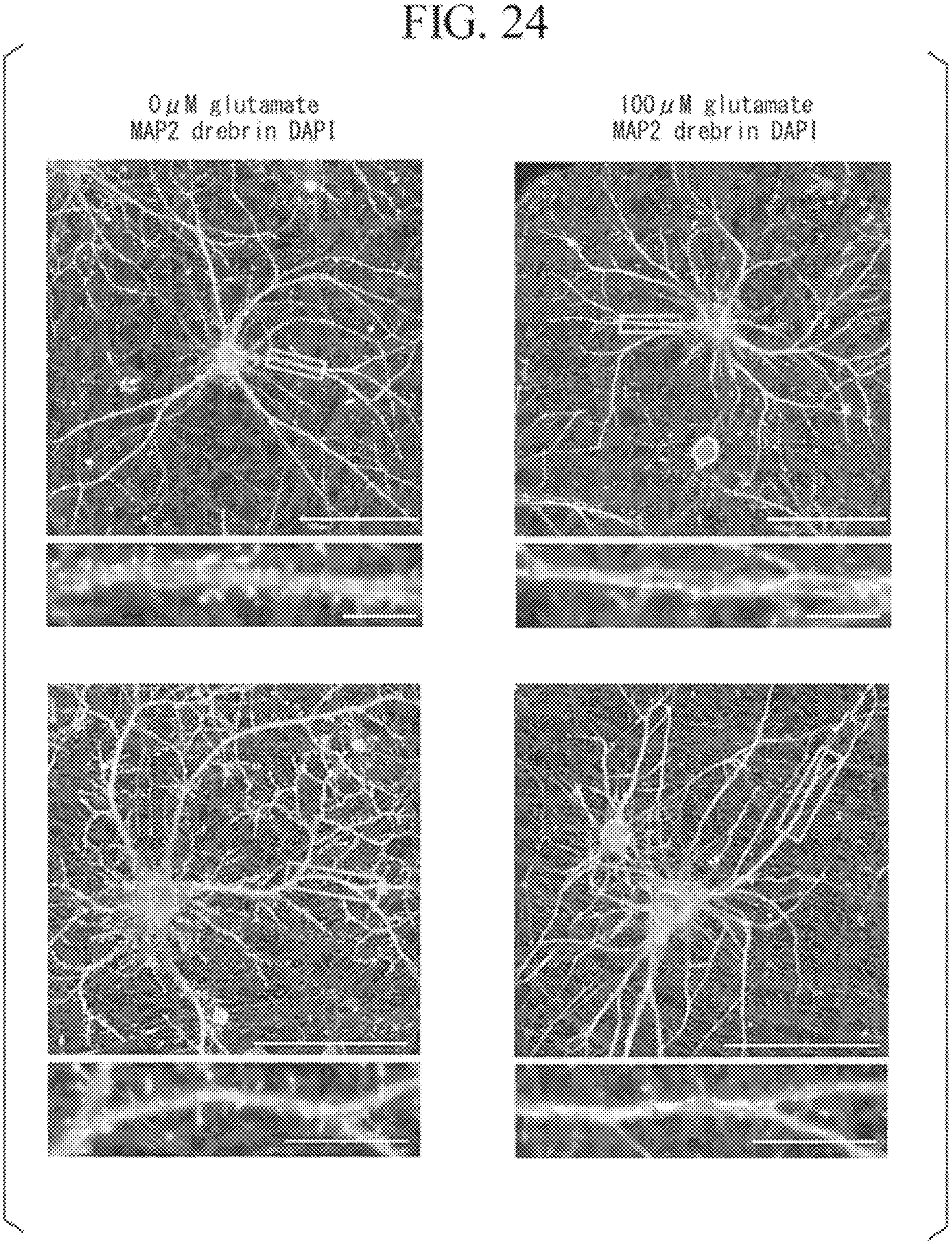
FIG. 24 shows representative fluorescence microscope images representing the results of immunostaining in Experimental Example 12.

FIG. 24 shows representative fluorescence microscope images representing the results of immunostaining. In FIG. 24, the left column shows the result of immunostaining without glutamic acid treatment, and the right column shows the result of immunostaining after treatment with 100 μM glutamic acid for 10 minutes.

In FIG. 24, the upper left and upper side is an image obtained by merging the staining results of MAP2, drebrin, and nuclei, and the upper left and lower side is an enlarged image of an area surrounded by a square of the upper left and upper side. The upper left and upper side scale bar is 100 μm and the upper left and lower side scale bar is 20 μm.

In addition, the lower left and upper side is an image obtained by merging the staining results of MAP2, drebrin, and nuclei on other cells, and the lower left and lower side is an enlarged image of an area surrounded by a square of the lower left and upper side. The lower left and upper side scale bar is 100 μm and the lower left and lower side scale bar is 20 μm.

The upper right and upper side is an image obtained by merging the staining results of MAP2, drebrin, and nuclei, and the upper right and lower side is an enlarged image of an area surrounded by a square of the upper right and upper side. The upper right and upper side scale bar is 100 μm and the upper right and lower side scale bar is 20 μm.

In addition, the lower right and upper side is an image obtained by merging the staining results of MAP2, drebrin, and nuclei on other cells, and the lower right and lower side is an enlarged image of an area surrounded by a square of the lower right and upper side. The lower right and upper side scale bar is 100 μm and the lower right and lower side scale bar is 20 μm.

As a result, in a case in which the human iPSC-derived mature stage 5 neurons were treated with 100 μM glutamate for 10 min, a phenomenon in which drebrin was effluxed from clusters in spines, and free drebrin migrated to the dendrite shaft ("drebrin exodus") was observed.

In rodents, it is known that in a case in which glutamate is added at a level at which neurons do not die, "drebrin exodus" is observed, and "synaptic toxicity" is induced. This is the first confirmation of synaptic toxicity in human neurons. In addition, this phenomenon is known to be an important mechanism of synaptic plasticity mediated by NMDA receptors, and it was found that synaptic plasticity could also possibly occur in the human iPSC-derived neurons.

This result indicates that the human iPSC-derived stage 5 neurons have normally functioning postsynapses.

Experimental Example 13

(Examination of Influence of Culture Medium Composition of Human iPSC-Derived Neurons)

Human iPSC-derived neurons were cultured in the same manner as in Experimental Example 1, except that various culture media whose compositions are shown in Table 2 below were used. Subsequently, cells were fixed on Day 77 and immunostained to evaluate whether stage 5 neurons were obtained. In Table 2 below, "NB Plus" represents NeuroBasal Plus (Thermo Fisher Scientific Inc.,) "BrainPhys" represents BrainPhys (StemCell Technologies), "B27 Plus" represents B-27 Plus (Thermo Fisher Scientific Inc.), "CDI" represents iCell nervous system supplement and iCell nerve supplement B (FUJIFILM Cellular Dynamics. Inc.), "CultureOne" represents CultureOne (Thermo Fisher Scientific Inc.), "DAPT" represents DAPT (CAS number: 208255-80-5), "–" represents without addition, and "+" represents with addition. The culture medium 2 in Table 2 below is the culture medium used in Experimental Example 1. In addition, "Spine OK" means that as a result of immunostaining described later, mature dendrites in which drebrin aggregated in spines to form clusters were formed, and indicates that stage 5 neurons were obtained. Also, "No spine" indicates that spines were not formed and stage 5 neurons were not obtained.

TABLE 2

| Culture medium | 1 | 2 | 3 | 4 | 5 | 6 | 7 |
|---|---|---|---|---|---|---|---|
| Basal medium | NB Plus | NB Plus | NB Plus | BrainPhys | BrainPhys | BrainPhys | BrainPhys |
| Major supplement | B27 Plus | B27 Plus | B27 Plus | CDI | CDI | CDI | B27 Plus |
| CultureOne | – | + | – | – | + | – | + |
| DAPT | – | – | + | – | – | + | – |
| Result of immunostaining on Day 77 | Spine OK | Spine OK | Spine OK | No spine | No spine | No spine | Spine OK |

Figure 25:
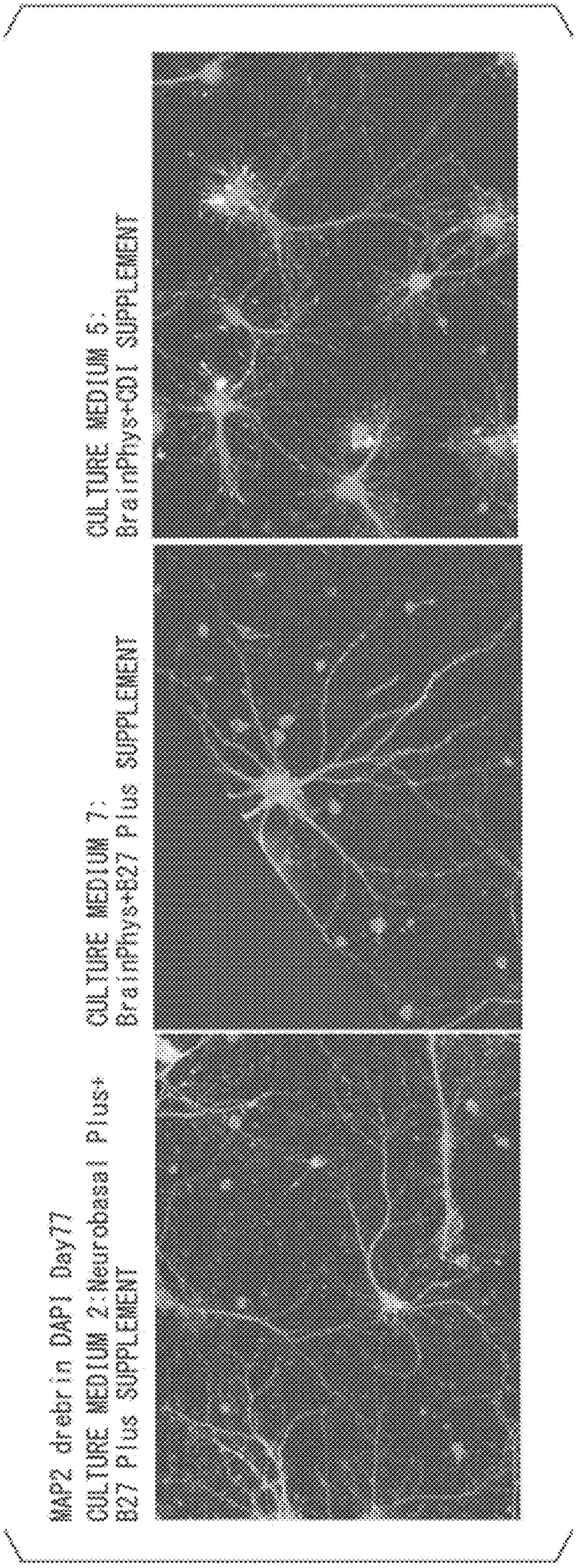
FIG. 25 shows representative fluorescence microscope images representing the results of immunostaining in Experimental Example 13.

FIG. 25 shows representative fluorescence microscope images representing the results of immunostaining of human iPSC-derived neurons cultured in each of the culture medium 2, medium 5, and medium 7 shown in Table 2 above.

As a result, in the culture medium 2 and the culture medium 7, dendrites were similarly matured, and drebrin clusters were observed. On the other hand, in the culture medium 5, it was observed that dendrite growth was poor, and many drebrin filopodia were generated, but did not mature into cluster-like spines. Table 2 above also shows the results of immunostaining in a case in which each culture medium was used.

These results indicated that it is important to add 8-27 Plus to the culture medium in order to obtain stage 5 neurons, and that the basal medium may be either Neurobasal Plus or BrainPhys.

Experimental Example 14

(Examination of Effect of Amount of B-27 Plus Added to Culture Medium of Human iPSC-Derived Neurons)

Human iPSC-derived neurons were cultured in the same manner as in Experimental Example 1. In Experimental Example 1, 2% of B-27 Plus (Thermo Fisher Scientific Inc.) was added to the culture medium, but in the present Experimental Example, the content was replaced with 4% of B-27 Plus or 10% of B-27 Plus. Subsequently, cells were fixed on Day 63 and immunostained to evaluate whether stage 5 neurons were obtained.

Figure 26:
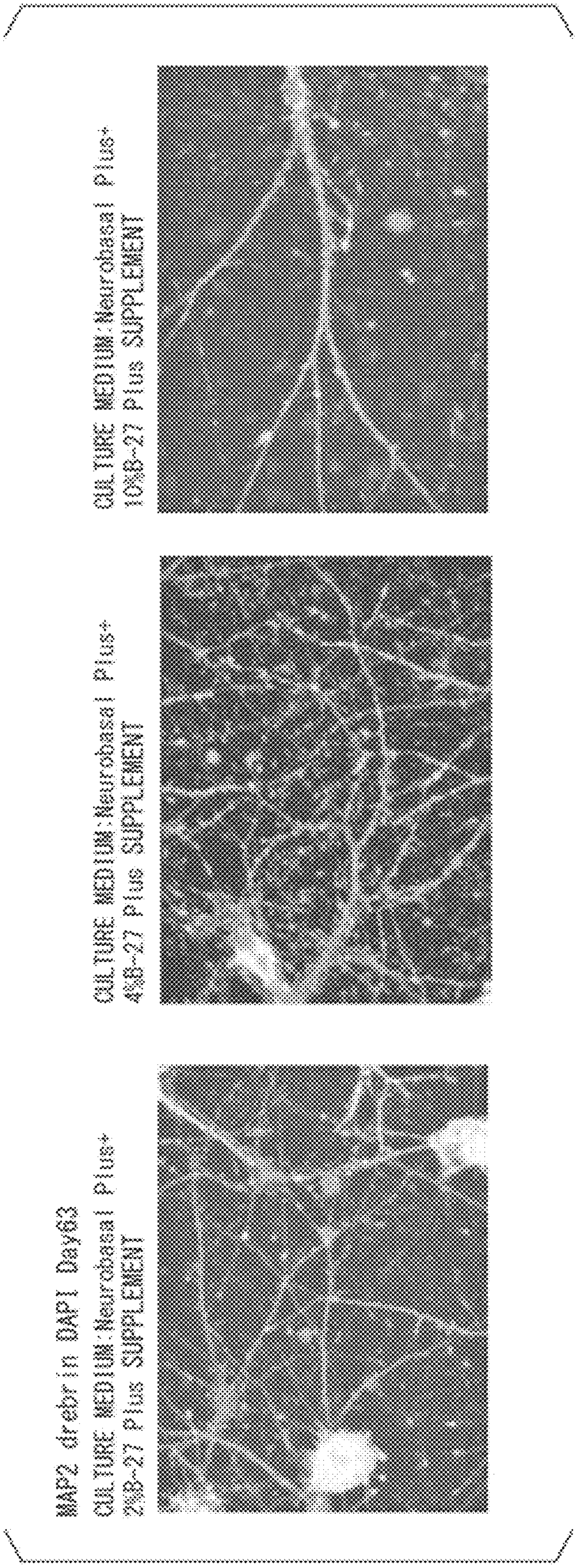
FIG. 26 shows representative fluorescence microscope images representing the results of immunostaining in Experimental Example 14.

FIG. 26 shows representative fluorescence microscope images representing the results of immunostaining of human iPSC-derived neurons cultured in culture media supplemented with 2% of B-27 Plus, 4% of 8-27 Plus, and 10% of B-27 Plus.

As a result, it was observed that dendrites matured, and accumulation of drebrin clusters began in all the culture medium compositions. However, it was observed that many filopodia still remained in 2% of B-27 Plus because the culture period was set to be one week shorter than the predicted completion time of maturation, drebrin was diffused around the neurites, and accumulation was not completed. Although many filopodia remained even in 4% of B-27 Plus, drebrin expression around the neurites seemed to be slightly increased. On the other hand, in 10% of B-27 Plus, many small granular drebrin clusters were observed, which suggested faster spine stabilization.

From the above results, it was found that in order to obtain stage 5 neurons, the amount of B-27 Plus added to the basal medium may be 2%, but the maturation efficiency to the stage 5 neurons increases as the amount is increased to 4% or 10%.

Experimental Example 15

(Preparation of Stage 5 Neurons from Neurological Disease Patient-Derived iPSCs)

A neural cell differentiation kit (product name: "Quick-Neuron (trademark) Excitatory-SeV Kit", ELIXIRGEN SCIENTIFIC, INC.) was used to prepare stage 3 neurons from healthy subject-derived iPSCs and neurological disease patient-derived iPSCs according to the manufacturer's protocol. The 1383D2 strain and 1231A3 strain were used as healthy subject-derived iPSCs. As neurological disease patient-derived iPSCs, the HPS3036 strain derived from Rett syndrome disease patients was used.

Thereafter, in the same manner as in Experimental Example 1, iPSC-derived neurons were cultured. Subsequently, cells were immunostained on Day 90, Day 91, and Day 112 to evaluate whether stage 5 neurons were obtained.

Figure 27:
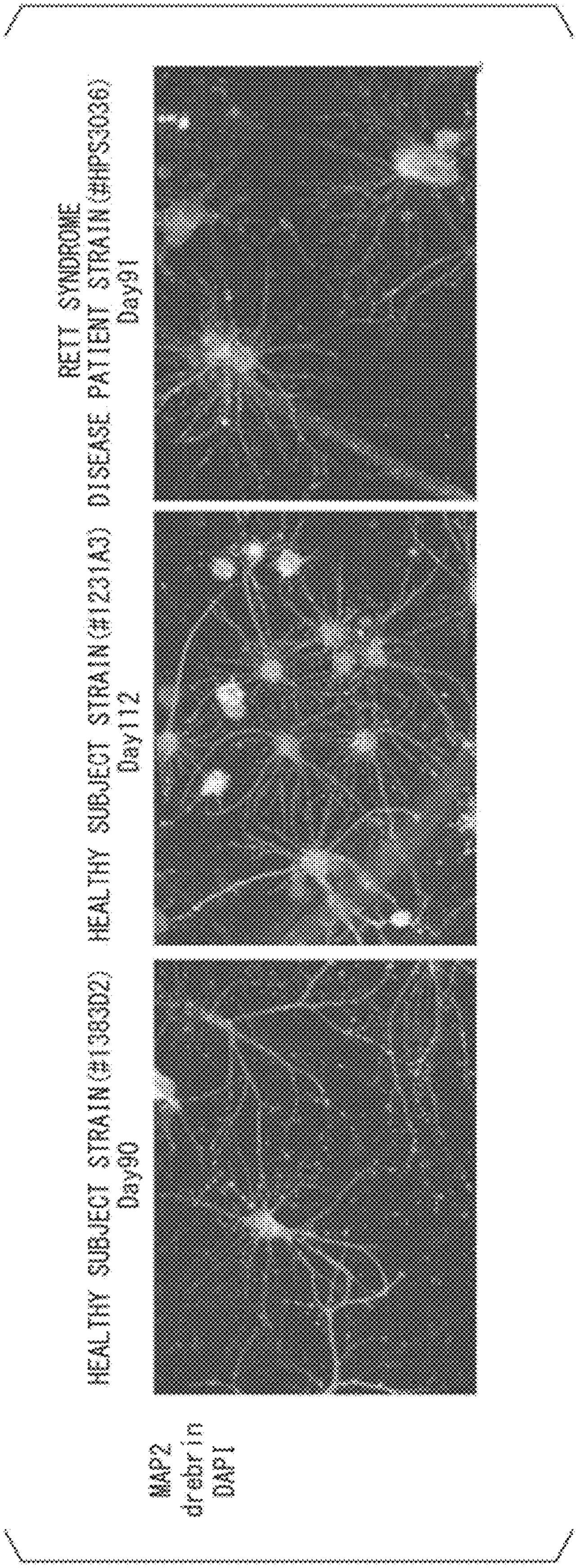
FIG. 27 shows representative fluorescence microscope images representing the results of immunostaining in Experimental Example 15

FIG. 27 shows representative fluorescence microscope images representing the results of immunostaining. The images were obtained by merging the staining results of MAP2, drebrin, and nuclei. As a result, the formation of drebrin clusters on or near dendrites was observed, and it was found that stage 5 neurons were obtained even in a case in which both the healthy subject-derived iPSCs and neurological disease patient-derived iPSC % were used.

The present invention includes the following aspects.

[1] A production method for stage 5 neurons with mature dendrites including a step of culturing stage 3 neurons with immature dendrites in a culture medium containing B-27 Plus.

[2] The production method according to [1], in which the stage 5 neurons have dendritic spines.

[3] The production method according to [1] or [2], in which a postsynaptic structure including drebrin and PSD95 is formed in the stage 5 neurons.

[4] The production method according to any one of [1] to [3], in which the stage 3 neurons express a neuronal marker including MAP2 and neurofilament heavy chain (NF-H) and are polarized.

[5] The production method according to any one of [1] to [4], in which the stage 3 neurons are obtained by differentiation induction of induced pluripotent stem cells (iPSCs).

[6] The production method according to [5], in which the stage 3 neurons are induced to differentiate by induction of expression of a transcription factor in the iPSCs.

[7] Stage 5 neurons with mature dendrites that are isolated and cultured in a container.

[8] A screening method for a therapeutic drug for a neurological disease including a step of culturing stage 3 neurons that are induced to differentiate from neurological disease patient-derived iPSCs in a culture medium containing 8-27 Plus in the presence of a test substance to obtain stage 5 neurons, and a step of assessing a phenotype of the stage 5 neurons, in which a case in which the phenotype of the stage 5 neurons in the presence of the test substance exhibits a phenotype more similar to a wild-type as compared with a phenotype of the stage 5 neurons in the absence of the test substance indicates that the test substance is a candidate of the therapeutic drug for the neurological disease.

[9] A screening method for a therapeutic drug for a neurological disease including a step of culturing stage 5 neurons that are induced to differentiate from neurological disease patient-derived iPSCs in the presence of a test substance in a predetermined period of time, and a step of assessing a phenotype of the stage 5 neurons, in which a case in which the phenotype of the stage 5 neurons in the presence of the test substance exhibits a phenotype more similar to a wild-type as compared with a phenotype of the stage 5 neurons in the absence of the test substance indicates that the test substance is a candidate of the therapeutic drug for the neurological disease.

PRIOR ART DOCUMENT

Patent Document

[Patent Document 1] Japanese Unexamined Patent Application, First Publication No. 2020-156463.

Non-Patent Document

[Non-Patent Document 1] Togo K., et al., Postsynaptic structure formation of human iPS cell-derived neurons takes longer than presynaptic formation during neural differentiation in vitro, Mol Brain 14:149, 2021.

While preferred embodiments of the invention have been described and illustrated above, it should be understood that these are exemplary of the invention and are not to be considered as limiting. Additions, omissions, substitutions, and other modifications can be made without departing from the scope of the invention. Accordingly, the invention is not to be considered as being limited by the foregoing description and is only limited by the scope of the appended claims.

What is claimed is:

1. A production method for stage 5 neurons with mature dendrites comprising:
- culturing stage 3 neurons with immature dendrites in a culture medium containing B-27 Plus;
- wherein the stage 3 neurons are obtained by differentiation induction of induced pluripotent stem cells (iPSCs).

2. The production method according to claim 1, wherein the stage 5 neurons have dendritic spines.

3. The production method according to claim 1, wherein a postsynaptic structure including drebrin and PSD95 is formed in the stage 5 neurons.

4. The production method according to claim 1, wherein the stage 3 neurons express a neuronal marker including MAP2 and neurofilament heavy chain (NF-H) and are polarized.

5. The production method according to claim 1, wherein the stage 3 neurons are induced to differentiate by induction of expression of a transcription factor in the iPSCs.

6. Stage 5 neurons with mature dendrites, comprising:

said stage 5 neurons being obtained by being isolated and cultured in a container; and said stage 5 neurons being obtained by differentiation induction of induced pluripotent stem cells (iPSCs).

* * * * *